US010959630B1

(12) United States Patent
Keller

(10) Patent No.: US 10,959,630 B1
(45) Date of Patent: Mar. 30, 2021

(54) DUAL AUDIOMETRIC PROBE HEADSET

(71) Applicant: MICRO AUDIOMETRICS CORPORATION, Murphy, NC (US)

(72) Inventor: James E. Keller, Murphy, NC (US)

(73) Assignee: MICRO AUDIOMETRICS CORPORATION, Daytona Beach, FL (US)

( * ) Notice: Subject to any disclaimer, the term of this patent is extended or adjusted under 35 U.S.C. 154(b) by 404 days.

(21) Appl. No.: 16/139,642

(22) Filed: Sep. 24, 2018

Related U.S. Application Data

(60) Provisional application No. 62/563,709, filed on Sep. 27, 2017.

(51) Int. Cl.

| | |
|---|---|
| ***A61B 5/03*** | (2006.01) |
| ***H04R 1/10*** | (2006.01) |
| ***H04R 5/04*** | (2006.01) |
| ***H04R 5/033*** | (2006.01) |
| ***H04R 3/00*** | (2006.01) |

(52) U.S. Cl.

CPC ............... *A61B 5/03* (2013.01); *H04R 1/105* (2013.01); *H04R 1/1016* (2013.01); *H04R 1/1033* (2013.01); *H04R 3/00* (2013.01); *H04R 5/0335* (2013.01); *H04R 5/04* (2013.01); *H04R 2201/109* (2013.01)

(58) Field of Classification Search

CPC combination set(s) only.

See application file for complete search history.

(56) References Cited

U.S. PATENT DOCUMENTS 3,882,848 A 5/1975 Klar
4,025,733 A * 5/1977 Klar ........................ H04M 1/05 2/171.2
4,029,083 A * 6/1977 Baylor ................. A61B 1/2275 600/559
4,057,051 A 11/1977 Kerouac
5,063,946 A 11/1991 Wada
5,197,332 A * 3/1993 Shennib ................. A61B 5/121 600/559
6,159,171 A 12/2000 Densert et al.
6,629,938 B1 10/2003 Engvall et al.
8,398,562 B2 3/2013 Keller
8,781,141 B2 7/2014 Higgins et al.
9,155,494 B2 * 10/2015 Iseberg ................ A61B 5/6817

(Continued)

FOREIGN PATENT DOCUMENTS

WO 9422372 3/1994

OTHER PUBLICATIONS

Non-Final Office Action, U.S. Appl. No. 16/139,486 (dated Jan. 21, 2021).

(Continued)

*Primary Examiner* — Fan S Tsang
*Assistant Examiner* — Angelica M McKinney
(74) *Attorney, Agent, or Firm* — Robinson IP Law, PLLC

(57) ABSTRACT

A hands-free dual audiometric probe headset. In one embodiment, the headset includes a resilient headband attached to a first audiometric probe holder including a first audiometric probe attached thereto and a second audiometric probe holder including a second audiometric probe attached thereto, the headset system configured to reliably hold the audiometric probes in place in the ears of a test subject during binaural testing.

14 Claims, 27 Drawing Sheets

(56) References Cited

U.S. PATENT DOCUMENTS

| | | | | |
|---|---|---|---|---|
| 9,615,778 | B2 | 4/2017 | Smith | |
| 10,492,011 | B1 | 11/2019 | Haynes et al. | |
| 2004/0037428 | A1 | 2/2004 | Keller | |
| 2004/0216947 | A1* | 11/2004 | Warring | A61B 5/6815 181/129 |
| 2006/0197412 | A1 | 9/2006 | Rasmussen | |
| 2009/0012420 | A1 | 1/2009 | Keller | |
| 2009/0321177 | A1 | 12/2009 | McMahon et al. | |
| 2018/0160972 | A1 | 6/2018 | Norgaard et al. | |
| 2020/0389741 | A1 | 12/2020 | Agac | |

OTHER PUBLICATIONS

Non-Final Office Action, U.S. Appl. No. 16/139,524 (dated Feb. 9, 2021).

* cited by examiner

DUAL AUDIOMETRIC PROBE HEADSET

PRIORITY

This application claims priority to U.S. Provisional Patent Application Ser. No. 62/563,709 to James E. Keller filed on Sep. 27, 2017 entitled "DUAL AUDIOMETRIC PROBE HEADSET SYSTEM", the content of which is incorporated herein by reference in its entirety.

FIELD

This disclosure relates to the field of audiometry. More particularly, this disclosure relates to a new audiometric dual probe headset system.

BACKGROUND

Audiometric probes are routinely used for several standard auditory tests. These include pure tone and speech audiometry, aural acoustic immittance (AAI) tests, and otoacoustic emission (OAE) tests. Insert earphones for audiometric testing require only a speaker, but probes for AAI and OAE are more complex. OAE testing requires two speakers to present independent signals to avoid intermodulation distortion, plus a microphone to monitor emitted sounds from the ear canal. Basic AAI probes contain one speaker, but diagnostic AAI probes may include two speakers (one for probe tone and one for higher level acoustic reflex eliciting signals). In addition, AAI probes contain a microphone for monitoring the probe tone, an air line port for varying ear canal air pressure, and a pressure transducer for monitoring ear canal air pressure.

Typically, instruments intended for a specific test use a probe optimized for that test. Efficient audiometric probe space utilization and availability of sophisticated electronics in small packages makes it possible to design a single probe capable of performing each of the audiometric tests described above. The challenge lies in properly securing a probe cuff in the concha of a test ear. AAI testing requires that an air tight seal be maintained between the ear cuff and the concha of the test subject. In addition, standard audiometry and OAE testing benefit from a probe sealed in the concha due to increased isolation from ambient noise. Each of these tests require consistent placement of the probe in the concha (test/retest reliability). When a single probe is used, it is typically held in the ear canal via a cuff that extends into the canal, with friction holding the cuff in place. Alternatively, the cuff is hand-held during testing. Both methods allow for variability in probe placement. For example, different testers may use different insertion or holding force of a probe in the concha of a test subject. For some test situations, such as pure tone testing with masking, or contralateral acoustic reflex testing, it is desirable to have a probe in place and consistently sealed at each ear.

What is needed, therefore, is an audiometric instrument and related method capable of holding a probe seated in each ear canal so that placement and insertion force are consistent and the ear cuff is sealed in the conchae of a user for AAI testing and provides noise immunity for standard audiometry and OAE testing.

SUMMARY

The above and other needs are met by a dual probe audiometric instrument configured for binaural audiometric testing with masking. Ideally, each probe would have a microphone, two speakers, probe and stimulus signal generation capability (e.g., via codec with built-in digital signal processing capability), facility for air pressure control (e.g., from an ear canal pressurization device), and a pressure transducer for monitoring pressure in the ear canal. Probes equipped in this manner would be capable of binaural audiometric pure tone or speech testing, binaural OAE testing, and binaural AAI testing. The probe microphone could also be used to implement self-monitoring of acoustic signals in the ear canal. Such probes would be capable of a broad variety of tests and could be utilized for a progressive test battery ranging from screening to diagnostic in a single test session, and with a single probe placement.

In one aspect, a dual probe audiometric headset is disclosed comprising (a) a resilient headband including a first end and a second end; (b) a pair of audiometric probe holders including a first probe holder attached proximate to the first end of the headband and a second probe holder attached proximate to the second end of the headband, each probe holder comprising (i) a shell defining a primary cavity for docking an audiometric probe in the primary cavity and attaching an audiometric probe to the probe holder; (ii) a pad located at a first end of the probe holder for resting the probe holder against the head of a user of the headset; and (iii) a pad arm extending from the shell to the first end of the probe holder. The pad provides a large surface area for contact with the head of a user, such surface area ranging in size from at least 6 $cm^2$ to about 10 $cm^2$. Preferably, the headband is larger than the head of a large adult human so that the only physical contact between the dual audiometric headset and the head of a user is via the probe holder pads and the pair of probes, with the probe holder pads preventing the dual audiometric headset from rotating on the head of a user. The resilient headband provides spring tension to force the probe holder pads and the pair of probes against the head of a user to form a substantially airtight seal with the ears of a user. Preferably, the headband is attached to specific locations along the pad arms so that more than 50% of the force exerted by the dual audiometric headset on the head of a user is exerted through the pads.

The dual audiometric probe headset may further comprise a first audiometric probe docked in the primary cavity of the first probe holder and attached to the first probe holder and a second audiometric probe docked in the primary cavity of the second probe holder and attached to the second probe holder.

The first probe holder may further comprise a first pair of probe holder grooves, the second probe holder may further comprise a second pair of probe holder grooves, the first audiometric probe may further comprise a first pair of lateral extensions (e.g., screws with screw heads exposed) extending laterally from the probe casing which mechanically engage with the first pair of probe holder grooves, and the second audiometric probe may further comprise a second pair of lateral extensions extending laterally from the probe casing which mechanically engage with the second pair of probe holder grooves.

In another aspect, the first end of the headband further comprises a hook shape for attaching the headband to the first probe holder and the second end of the headband further comprises a hook shape for attaching the headband to the second probe holder.

In one embodiment, each probe holder further comprises a pad arm aperture through which an end of the headband can be inserted and a substantially cylindrical hook catch cylinder located inside the pad arm wherein the hook shaped first end of the headband is connected to and partially around the hook catch cylinder of the first probe holder, and wherein the hook shaped second end of the headband is connected to and partially around the hook catch cylinder of the second probe holder.

In a related embodiment, the pad arm aperture of the first probe holder is a long and narrow aperture long enough to permit the first probe holder to rotate about the hook catch cylinder of the first probe holder relative to the hook shaped first end of the headband, and wherein the pad arm aperture of the second probe holder is a long and narrow aperture long enough to permit the second probe holder to rotate about the hook catch cylinder of the second probe holder relative to the hook shaped second end of the headband.

In yet another embodiment, each audiometric probe comprises a plurality of substantially equally spaced protrusions oriented along an outer surface of each audiometric probe and each probe holder further comprises a plurality of substantially equally spaced indentations inside the primary cavity of each probe holder along an inner surface of each probe holder wherein the plurality of protrusions are shaped to mechanically engage with the plurality indentations so that the first audiometric probe can be selectively adjusted to different stationary positions relative to the first probe holder and the second audiometric probe can be selectively adjusted to different stationary positions relative to the second probe holder.

The dual audiometric headset may further comprise a first cable, a second cable and a main body including a controller wherein the first probe is connected to and in electrical communication with the controller via the first cable and wherein the second probe is connected to and in electrical communication with the controller via the second cable. In a related embodiment, the main body further comprises an air pressurization device in electrical communication with the controller and wherein the first probe is in direct fluid communication with the air pressurization device via the first cable and wherein the second probe is in direct fluid communication with the air pressurization device via the second cable. In a related embodiment, the dual audiometric headset may further comprise a first cable, a second cable, a base cable and a main body wherein the first cable and the second cable are jointly connected proximate to a first end of the base cable, and wherein the main body is attached proximate to a second end of the base cable, the main body including a controller wherein the first probe is connected to and in electrical communication with the controller via the first cable and base cable and wherein the second probe is connected to and in electrical communication with the controller via the second cable and the base cable.

The summary provided herein is intended to provide examples of particular disclosed embodiments and is not intended to cover all potential embodiments or combinations of embodiments. Therefore, this summary is not intended to limit the scope of the invention disclosure in any way, a function which is reserved for the appended claims.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

The figures are provided to illustrate concepts of the invention disclosure and are not intended to embody all potential embodiments of the invention. Therefore, the figures are not intended to limit the scope of the invention disclosure in any way, a function which is reserved for the appended claims.

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Adjacent: a first feature is said to be adjacent to a second feature if the first feature is directly on or otherwise attached to the second feature or in close proximity to the second feature such as being separated by one or more layers of other material.

Air or Gas: broadly defined as any gas or mixtures thereof

Direct Fluid Communication: a first feature is said to be in direct fluid communication with a second feature if there is a conduit or path for air to flow between the first feature and the second feature.

Electrical Communication: a first feature is said to be in electrical communication with a second feature if there is a conductive path for electricity in any form (including data transmission) to flow between the first feature and the second feature thereby electrically connecting the first feature with the second feature.

Proximate: a first feature is said to be proximate to a second feature if the first feature is attached to or otherwise extends all the way to the second feature or if the first feature is located close to or extends to a location close to the second feature.

Substantially Planar (or Substantially Flat): a characteristic of a surface that appears to be flat from the eye of an observer without the use of any magnifying viewing equipment.

Figure 1:
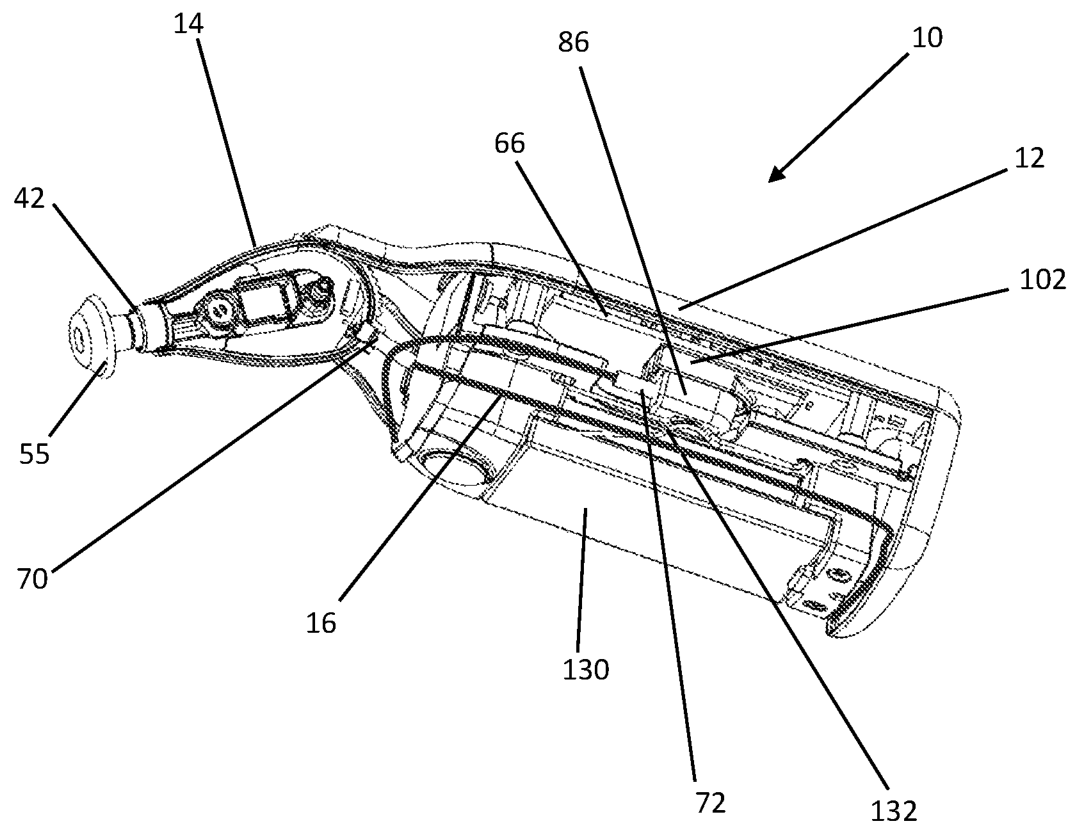
FIG. 1 shows a perspective view of an audiometric instrument including a main body, a controller board situated within a housing of the main body, a probe, and a cable connecting the flow of air and electricity from the main body to the probe.

FIG. 1 shows a perspective view of an audiometric instrument 10 including a main body 12 and a probe 14. Outer casing portions of the audiometric instrument 10 have been removed to better illustrate the features found inside the audiometric instrument 10. The probe 14 is physically connected to the main body 12, preferably using a hinge type attachment so that the probe 14 is free to rotate relative to the main body 12. Preferably, the audiometric instrument is also physically configured so that the probe 14 can be disengaged and pulled away from the main body 12 leaving only a cable 16 connecting the probe 14 with the main body 12. The probe 14 includes air channels and/or tubes as well as electrical components. The various air channels and/or tubes are in direct fluid communication with one or more features of the main body 12 via the cable 16 which includes space for air to flow through the cable 16. The electrical components of the probe 14 are in electrical communication with one or more features of the main body via wires 18 extending through the cable 16.

Figure 2:
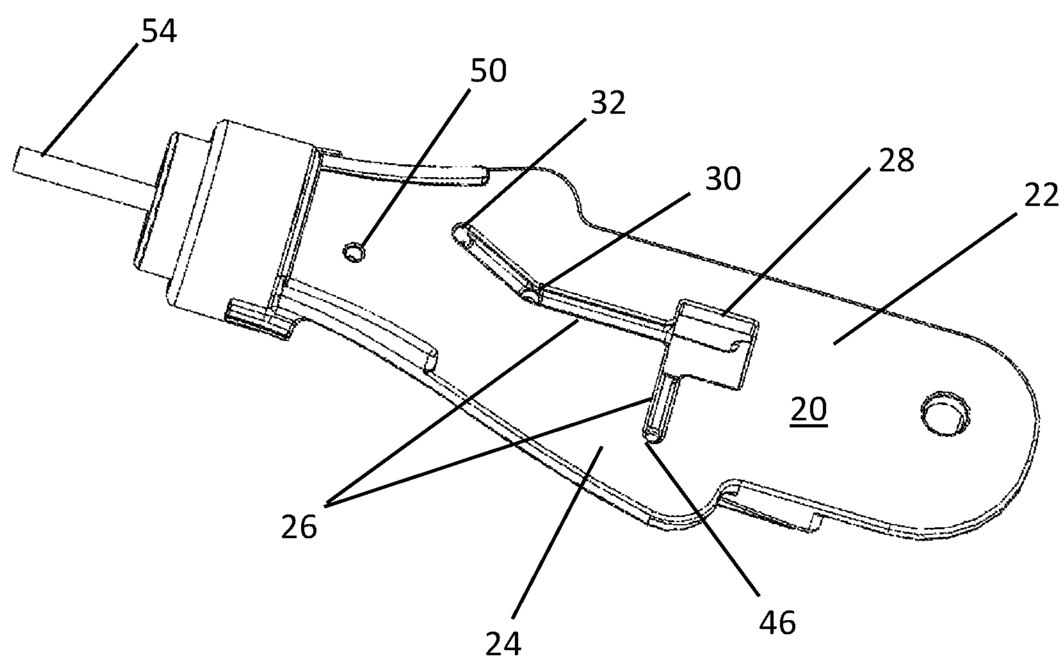
FIG. 2 shows a drawing of a first side of a probe core first body of an audiometric probe including a channel located along the first side of the probe core first body.

FIG. 2 shows a first side 20 of a probe core first body 22 which forms part of the audiometric probe 14. At least a portion of the first side 20 of the probe core first body 22 is preferably substantially planar (i.e., the substantially planar portion 24 of the first side 20 of the probe core first body 22). The first side 20 of the probe core first body 22 may include more than one substantially planar sections, but the substantially planar portion 24 preferably includes a probe core first body channel 26 formed therein extending from a first aperture 28 to a second aperture 30 and then to a third aperture 32. With reference to FIG. 2 and FIG. 3C, the first aperture 28 is provided as an access port for a first transducer 34 located adjacent to a second side 36 of the probe core first body 22, and for a first pressure transducer 38. In this embodiment, the first transducer 34 is an acoustic reflex eliciting signal speaker. The second aperture 30 is provided as a port for a second transducer 40 located adjacent to the second side 36 of the probe core first body 22. In this embodiment, the second transducer 40 is a probe tone speaker.

The probe core first body channel 26 extends proximate to a probe tip 42. In this particular embodiment, the probe core first body channel 26 extends to the third aperture 32 which leads to a tunnel 44 located on the second side of 36 of the probe core first body 22. The tunnel 44 then extends proximate to the probe tip 42 allowing for direct fluid communication between the first transducer 34, the second transducer 40 and the probe tip 42 which would interface with a user's ear when the audiometric instrument 10 is in use. In certain other embodiments, the probe core first body channel 26 extends all the way to a location where the probe core first body 22 interfaces with the probe tip 42. The probe core first body channel 26 further extends in a different direction beyond the first aperture 28 to a fourth aperture 46 which leads to an air line pipe 48 in fluid communication with the cable 16 via connecting tubing 49 for providing pressure (either positive or negative) along the probe core first body channel 26.

Figure 3A:
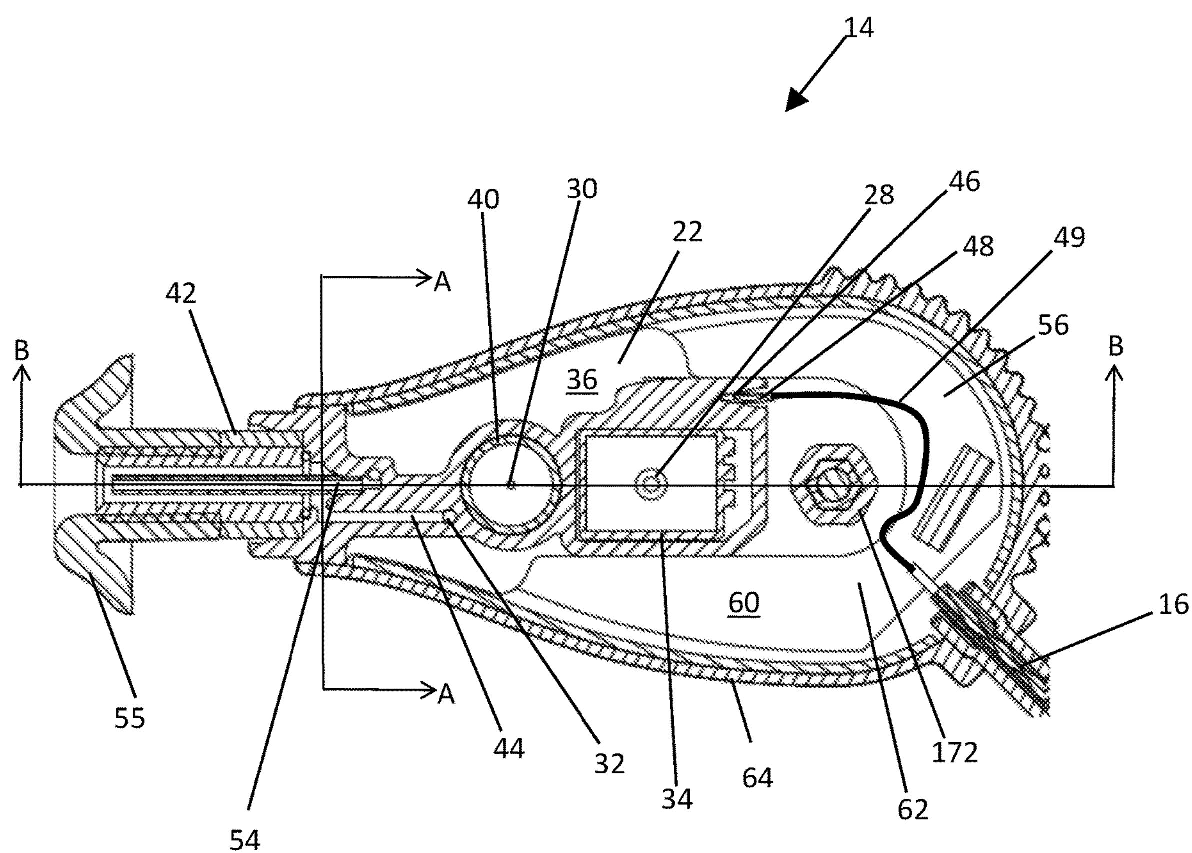
FIG. 3A shows a cross-sectional drawing of an audiometric probe showing a second side of the probe core first body shown in FIG. 2, the audiometric probe further including a probe tip, a probe core second body attached adjacent to the probe core first body and a protective outer casing.
Figure 3B:
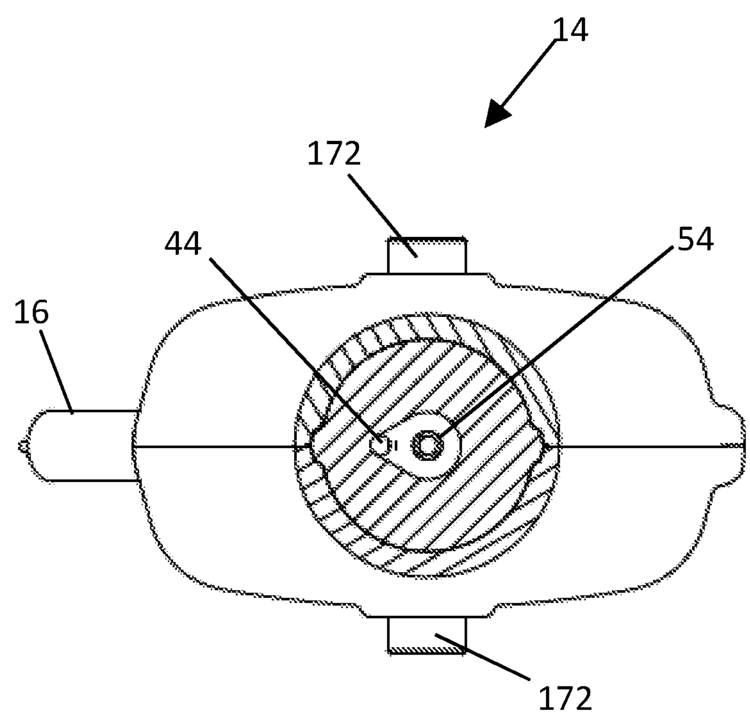
FIG. 3B shows a cross-sectional drawing of an end view of the audiometric probe shown in FIG. 3A taken along line A-A of FIG. 3A.
Figure 3C:
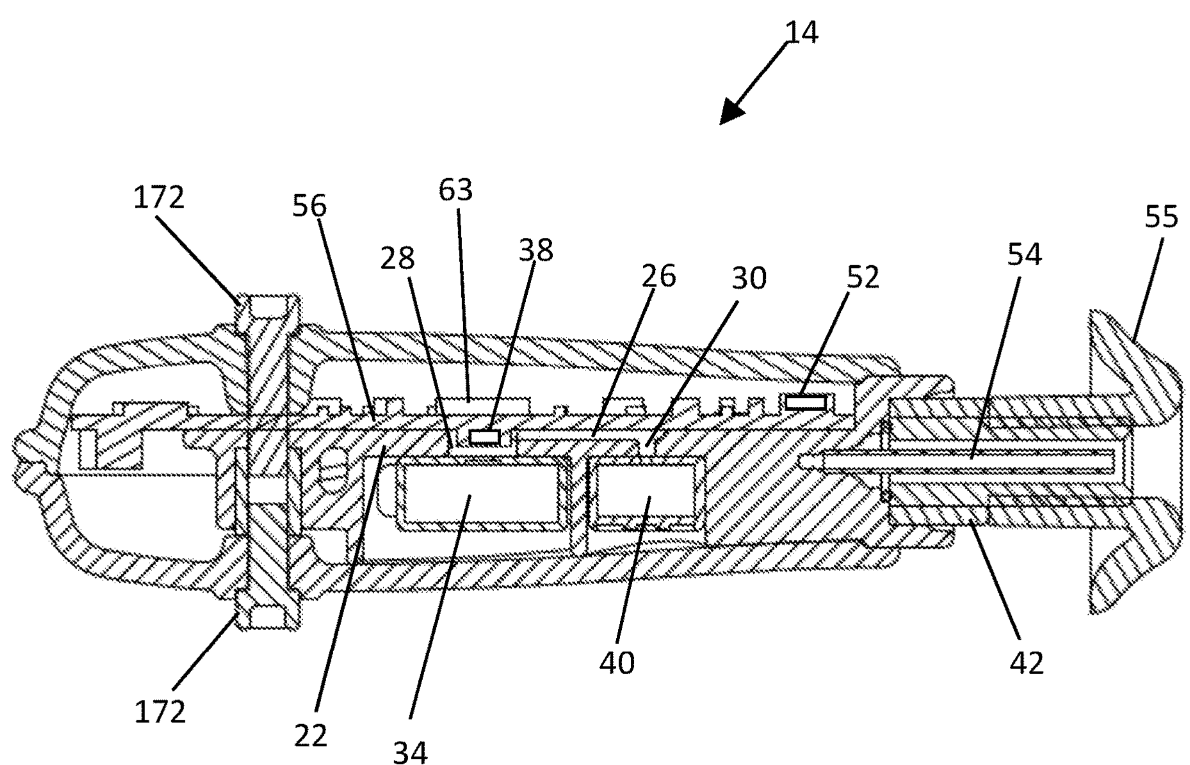
FIG. 3C shows a cross sectional drawing of a plan view of the audiometric probe shown in FIG. 3A taken along line B-B of FIG. 3A showing various components including a first pressure transducer.
Figure 4:
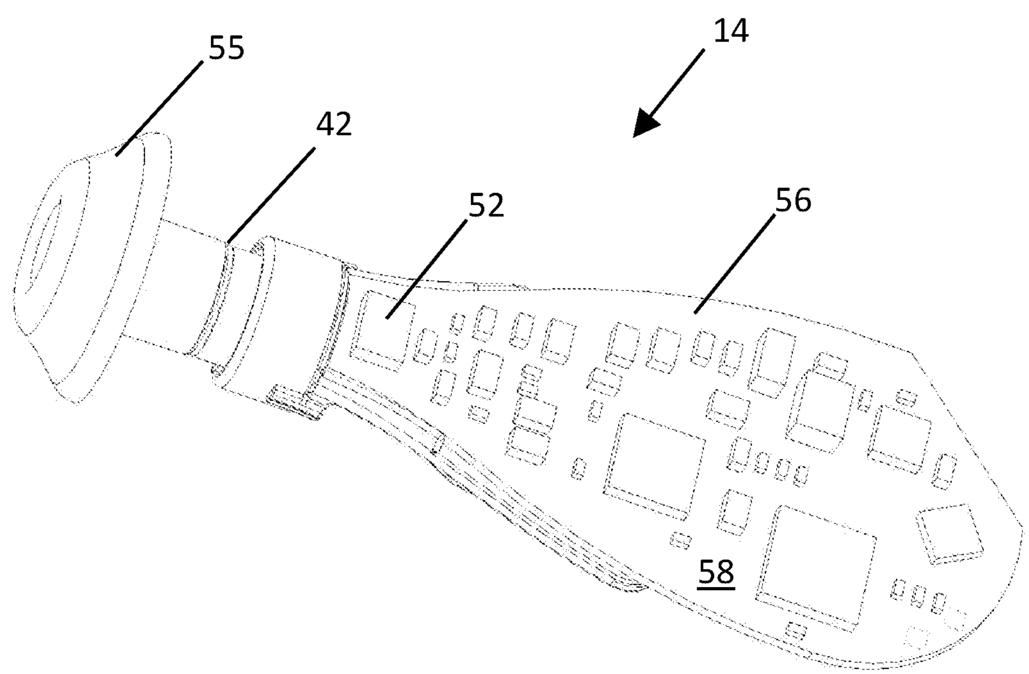
FIG. 4 shows a drawing of a first side of the probe core second body attached to the probe core first body shown in FIG. 2.
Figure 5:
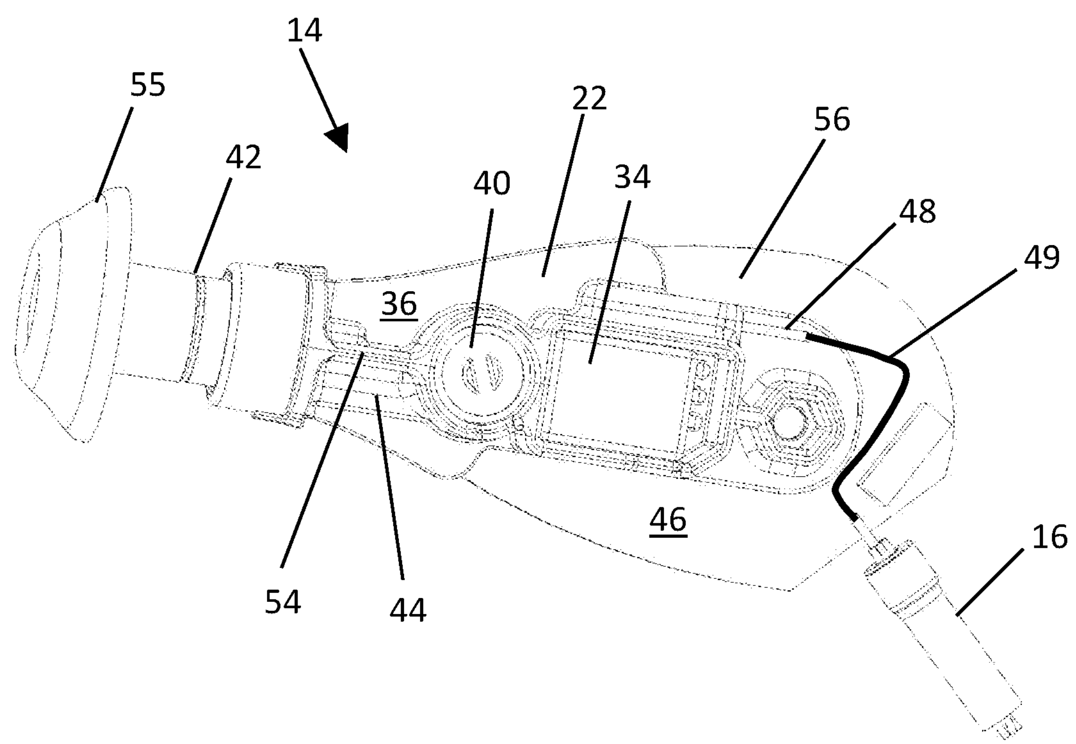
FIG. 5 shows a drawing of the second side of the probe core first body shown in FIG. 2 and further including a first transducer and a second transducer.

With reference to FIGS. 2-4, a fifth aperture 50 is located proximate to the probe tip 42 to act as a port for a microphone 52 attached adjacent to the probe core first body 22. The fifth aperture 50 leads to a tube 54 along the second side 36 of the probe core first body 22 wherein the tube 54 preferably extends into the probe tip 42, thereby providing direct fluid communication between the microphone 52 and the probe tip 42 (including an associated ear cuff 55). In the embodiment shown in FIGS. 2-4, the fifth aperture 50 extends through the probe core first body 22 and then through a probe core second body 56 including a first side

58 on which the microphone 52 is mounted. In the embodiment shown, the probe core second body 56 comprises a printed circuit board.

With reference to FIGS. 2-5, the probe core second body 56 includes a second side 60 wherein at least a portion of the second side 60 of the probe core second body 56 is substantially planar (i.e., the substantially planar portion 62 of the second side 60 of the probe core second body 56). The substantially planar portion 62 is preferably sandwiched against the substantially planar portion 24 of the first side 20 of the probe core first body 22, thereby converting the probe core first body channel 26 into a cavity through which sound and pressure may be transmitted. When in use, the cavity created along the probe core first body channel 26 is substantially sealed (except for specific locations along the cavity) so that the pressure along the probe core first body channel 26 can be controlled by a pressurization device located in the main body 12 which is in fluid communication with the cable 16, the connecting tubing 49, and the air line pipe 48. The first pressure transducer 38 is mounted on the second side 60 of the probe core second body 56. Pressure control in an audiometric probe through tubing (as opposed to cavities) is known in the art so no details regarding how the pressure is controlled are provided herein. However, it is noted that the probe core first body channel 26 operates like a tube when the probe core first body 22 and the probe core second body 56 are attached together but without the negative drawbacks from using a tube. Such attachment is preferably made using glue to attach at least a portion of the first side 20 of the probe core first body 22 with at least a portion of the second side 60 of the probe core second body 56. However, other means of attaching the probe core first body 22 to the probe core second body 56 are considered a part of this disclosure.

Figure 6:
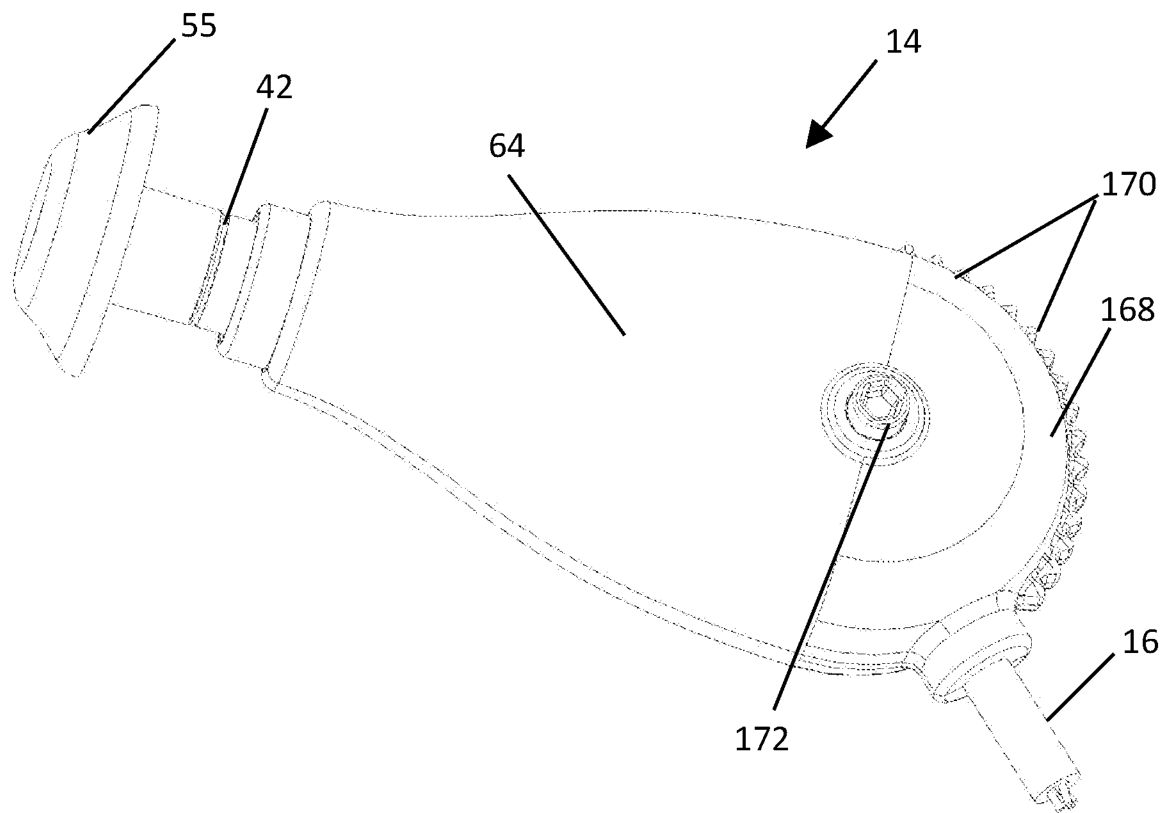
FIG. 6 shows a drawing of the apparatus shown in FIGS. 2-5 including a protective outer casing preferably held in place by a screw.

Power and control leads preferably extend through the probe core first body 22 from the probe core second body 56 (e.g., a printed circuit board) to features located on the second side 36 of the probe core first body 22 such as, for example, the first transducer 34 and the second transducer 40. Other electronic components may be included on the probe core second body 56 including components to control the operation of the audiometric probe 14 including a probe controller 63. Alternatively, control can be provided from a source external to the audiometric probe 14 and sent through the wires 18 in the cable 16 form the main body 12 to the probe 14. Power is provided from a battery 130 or other power source external to the audiometric probe 14 and sent through the wires 18 in the cable 16 form the main body 12 to the probe 14. The probe 14 preferably includes an outer casing 64 to surround and protect the internal components of the probe 14 as shown in FIG. 6.

In the embodiment shown in FIGS. 2-6, various features of the audiometric probe 14 use the same channel to transmit sound and pressure, such features including the first transducer 34, the first pressure transducer 38, and the second transducer 40. This configuration is desirable because it makes very efficient use of space in the probe 14 and along the probe core first body 22 by connecting various features to the same channel. However, in other embodiments, separate channels may be used. For example, an embodiment could include two channels wherein a first channel connects a transducer to a probe tip and wherein a separate second channel connects air pressure control features to the probe tip. In other examples, multiple channels can be used in a single probe. For example, a channel could be routed from a speaker port to a probe tip, from a probe tip to a microphone, from a pressure source to a pressure transducer, and various other combinations. As with the example shown in FIG. 2, single channels can connect two or more audiometric probe features. Single channels connecting four, five and more features are also considered a part of this disclosure. Persons having ordinary skill in the art will appreciate that a very large number of combinations of channels connecting audiometric probe features are possible and the specific examples provided in this disclosure are not intended to limit such possible combinations. Channels can be formed (e.g., routed) from any first point to any other point along the probe core first body 22, providing flexibility in transducer placement. Channels take up virtually no space in the audiometric probe 14, and may be changed as needed for different or newer models of audiometric probes. For example, there may be changes made to the parts layout of a printed circuit board to be used in an audiometric probe requiring one or more differently formed channels in a probe core first body attached to the printed circuit board, such channels corresponding to the locations of parts on the printed circuit board. Channels in a plastic probe core first body (e.g., the probe core first body 22 disclosed herein) make it possible to create channels that cannot be done successfully using plastic tubing due to space constraints, intervening structures in the way, or concerns about kinking of plastic tubing. Plastic tubing can also become brittle over time and prone to breakage or cracking, which, in turn, can lead to acoustic leaks and need for repair. Channels in the plastic main bodies of probes do not have these problems which are significant advantages to the embodiments of audiometric probes described herein.

In addition to the embodiments of the audiometric probe 14 described above, a method is disclosed wherein the method includes the step of sending a first transmission through a cavity formed between a probe core first body and a probe core second body of an audiometric probe. The first transmission could be a sound transmission from a transducer and/or a gas pressure transmission from a gas pressure control source in fluid communication with the cavity. A "gas pressure transmission" referred to herein can include an increase in pressure and/or a decrease in pressure inside the cavity or multiple fluctuations in pressure. The transmission is made from a first audiometric probe feature to a second audiometric probe feature. For example, the first audiometric probe feature includes a transducer (e.g., a speaker) and the second audiometric probe feature includes an audiometric probe tip. Alternatively, for example, the first audiometric probe feature may include a microphone, a pressure control apparatus, or a pressure transducer. The method described herein does not require plastic tubing for internal connections of features in an audiometric probe.

Channels such as the probe core first body channel 26 shown in the figures can be formed in the substantially planar portion of the first side 20 of the probe core first body 22. With reference to the figures as an example, a method of making an audiometric probe is disclosed including a step of fabricating a probe core first body 22 for use in an audiometric probe wherein the probe core first body includes a substantially flat surface. A second step includes forming (e.g., routing) one or more channels 26 along the substantially flat surface. The channels are preferably small diameter semi-circular channels. Such routing can be accomplished using, for example, 3D printing techniques known to persons having ordinary skill in the art. Alternatively, the probe core first body 22 may be molded or machined using, for example, a CNC machine. The probe core first body is preferably made of plastic or other polymer-based material. Unless otherwise specified, other parts of the probe other than electrical parts are preferably made of plastic or other polymer-based material. In one example, the channels are created during 3D printing or by the mold used to make the probe core first body 22. The channels are made to lie along the needed sound/pressure paths in the flat surface of the probe core first body 22 from a source (e.g., a transducer 34) to a destination (e.g., a probe tip 42). A third step of the method of making an audiometric probe includes attaching a substantially flat surface 62 of a probe core second body 56 to the substantially flat surface 24 of the probe core first body 22 to form a cavity along the one or more channels 26 between the probe core first body 22 and the probe core second body 56. Another step may include attaching one or more features adjacent to the probe core first body so that the one or more features are in fluid communication with one another along the one or more channels 26. For example, a transducer 34 may be attached adjacent to the probe core first body 22 including power and control leads wherein the transducer 34 is in fluid communication with a different feature (e.g., a probe tip 42) along the one or more channels 26. The air line pipe 48 may be attached adjacent to the probe core first body 22 wherein the air line pipe 48 is in fluid communication with a pressure control feature and one or more of the one or more formed channels 26. Additionally or alternatively, a further step may include attaching one or more features adjacent to the probe core second body 56. For example, a microphone 52 may be attached adjacent to the probe core second body 56.

Figure 7:
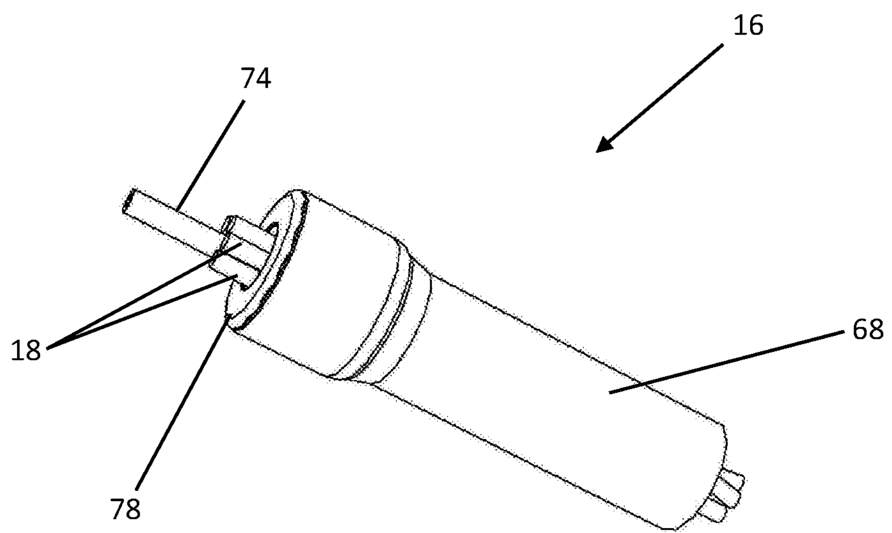
FIG. 7 shows a perspective view of a first end of the cable from FIG. 1 including a first pipe and wires protruding from the first end of the cable, a shroud, an eyelet cap inserted into the end of the shroud, and void space within the shroud.
Figure 8:
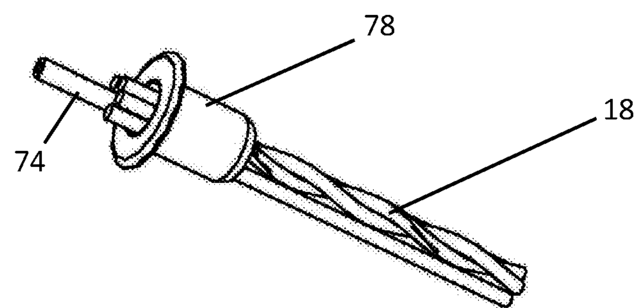
FIG. 8 shows a perspective view of the first end of the cable shown in FIG. 7 with the shroud removed, revealing the eyelet cap, pipe, wires and void space within the shroud.
Figure 9:
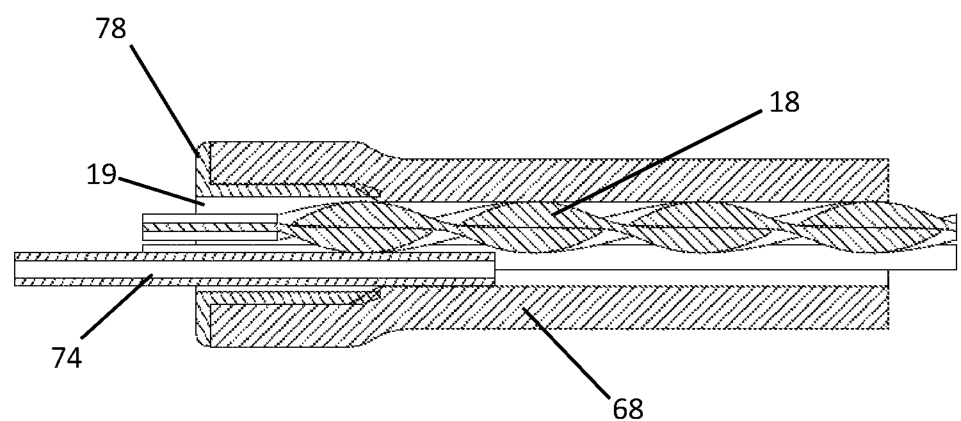
FIG. 9 shows a cross-sectional view of the first end of the cable shown in FIG. 7 and FIG. 8.

In a preferred embodiment, with reference back to FIG. 1, the cable 16 provides a flow path for both electricity/electric signals and air to the probe 14 from a controller board 66 (including a system controller 67) in the main body 12 without the use of a separate air tube. In prior art devices, such cables include wires and a tube through which air can flow wherein the wires and the tube are bundled together. Such tubes are bulky and prone to kinking causing an overall audiometric device to fail to operate and requiring repairs. The preferred cable 16, a portion of which is shown in FIGS. 7-9, does not include a separate tube through which air can flow. Rather, the cable 16 includes wires 18 and a shroud 68 surrounding the wires 18 wherein some void space within the shroud 68 (a "shroud void" 19) remains between the two or more wires 18 and the shroud 68. Air is free to flow through the cable 16 inside the shroud 68 from one end of the cable (a probe end 70) to the other end of the cable (a controller end 72). The presence of the wires 18 inside the shroud 68 minimize the chance for kinking along the air flow path. FIG. 7 shows the probe end 70 of the cable 16 including the shroud 68 whereas FIG. 8 shows the probe end 70 of the cable 16 with the shroud 68 removed exposing the wires 18. The shroud is preferably made of rubber, plastic or other polymer-based material.

Figure 10:
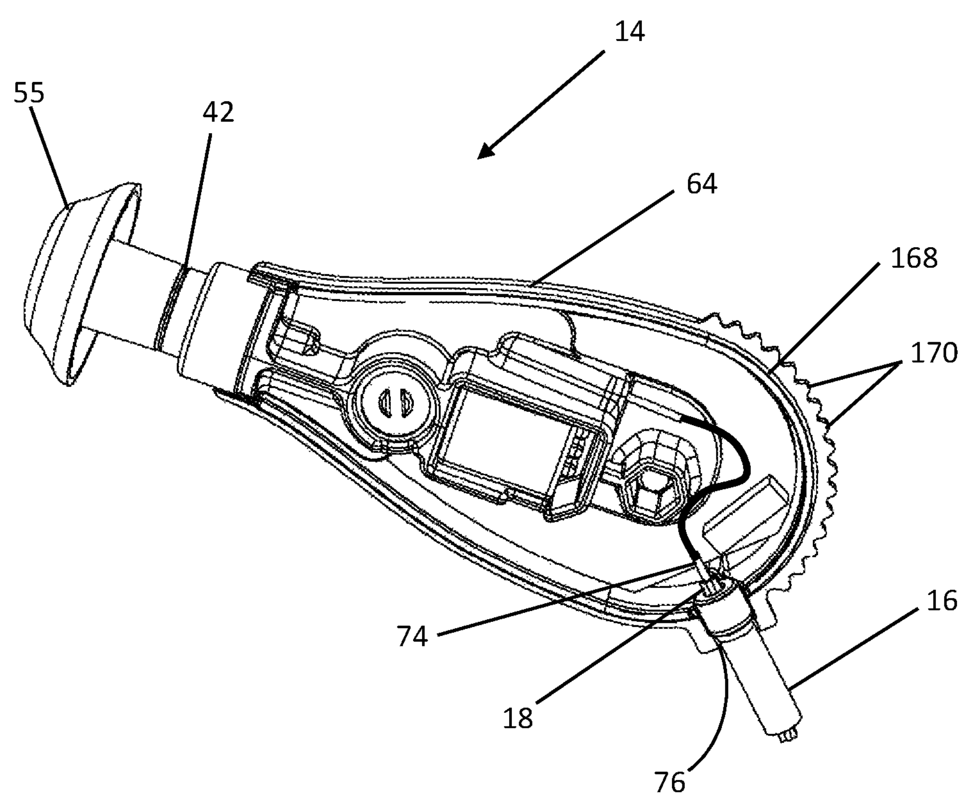
FIG. 10 shows a side view of the probe with a probe cover removed and with the first end of the cable from FIGS. 1, 3A, and 5-9 attached proximate to the probe.

FIG. 7 shows a close-up view of the probe end 70 of the cable 16 including a probe pipe 74 extending from the shroud void past the probe end 70. The probe pipe 74 is preferably a small metal pipe and the remainder of the probe end 70 is substantially sealed proximate to where the probe end 70 is attached adjacent to the probe 14. Liquid resin, wax, or other suitable material can be used to seal the probe end 70. As shown in FIG. 10, the probe end 70 is attached proximate to an outer casing aperture 76 in the probe outer casing 64 and preferably is held in place because the outer casing aperture 76 of the probe outer casing 64 is smaller than the probe end of the cable 70 due to an eyelet cap 78, preferably made of metal, which expands the shroud 68 diameter at the probe end 70 of the cable 16. Preferably, the probe end 70 is further secured in place in the probe casing 64 using liquid resin, wax, or other suitable material. The probe pipe 74 is connected to and in fluid communication with the connecting tubing 49. Through one or more tubes and/or channels (not shown) in the probe 14 (e.g., the air line pipe 48, the connecting tubing 49 and the probe core first body channel 26), the probe pipe 74 is in direct fluid communication with the probe tip 42 of the probe 14 such that air flow and pressure can be controlled from the controller board 66 controlling a pressurization device 82 all the way to the probe tip 42 where the audiometric instrument 10 including the ear cuff 55 is shaped to interface with the ear of a user. An example of such a pressurization device 82 is the Ear Canal Pressurization Device disclosed in U.S. Pat. No. 8,398,562 available from Micro Audiometrics Corporation based in Murphy, N.C.

Figure 11:
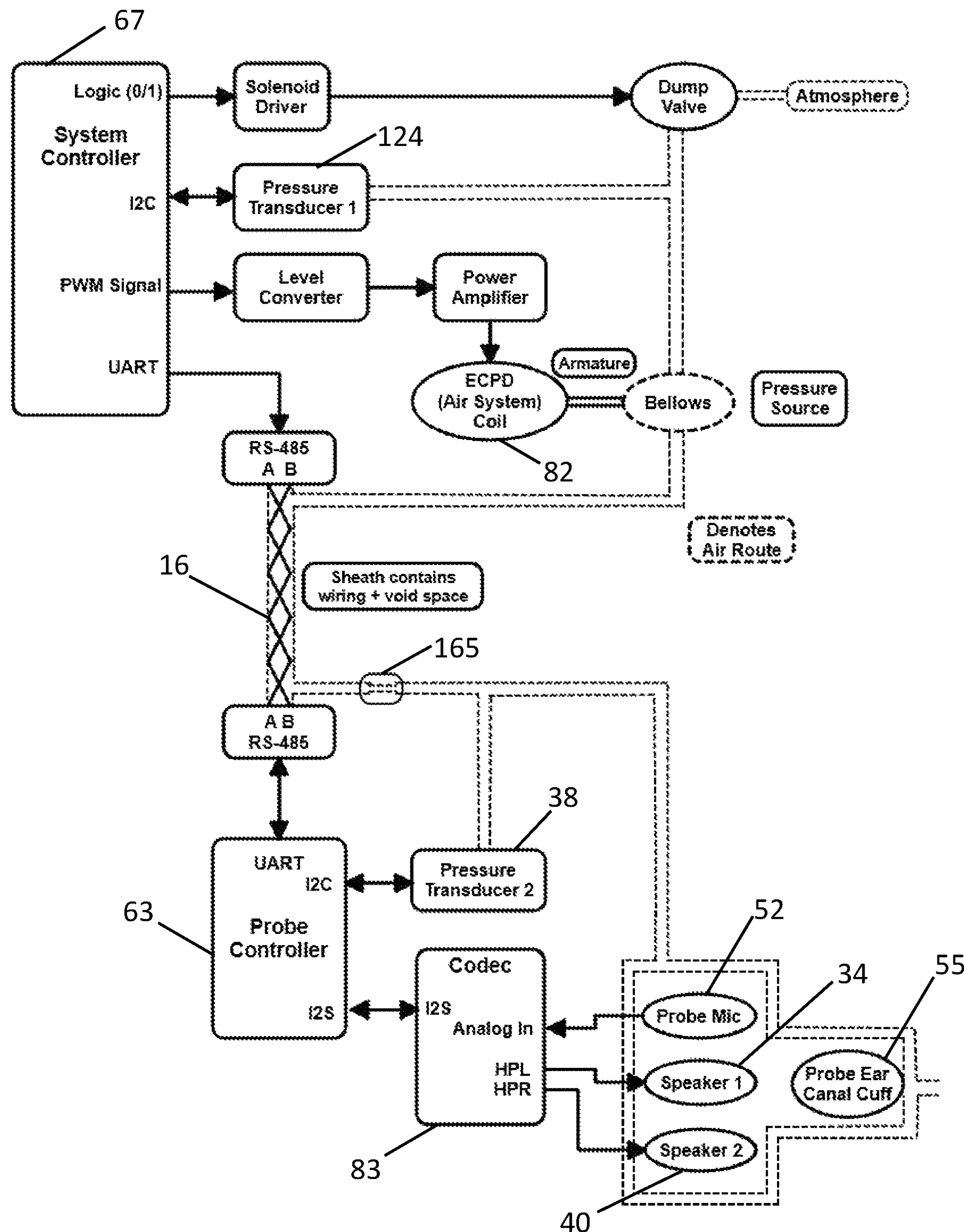
FIG. 11 shows a schematic of the audiometric instrument showing electrical connections and air flow pathways.

Although the wires 18 are shown as being cut off for illustrative purposes after entering the probe outer casing 64, the wires 18 actually extend into the probe 14 and are in electrical communication with one or more features of the probe 14 such as, for example, a coder-decoder (or "codec") 83, one or more speakers, one or more microphones, and/or one or more transducers. FIG. 11 shows a schematic of a preferred embodiment of the audiometric instrument 10 showing electrical connections as arrows and showing air flow paths as linear areas bounded by dashed lines. The various electrical components described including controllers, speakers, codec, pressure transducers and microphone are well known to persons having ordinary skill in the art and are not discussed in further detail here.

Figure 12:
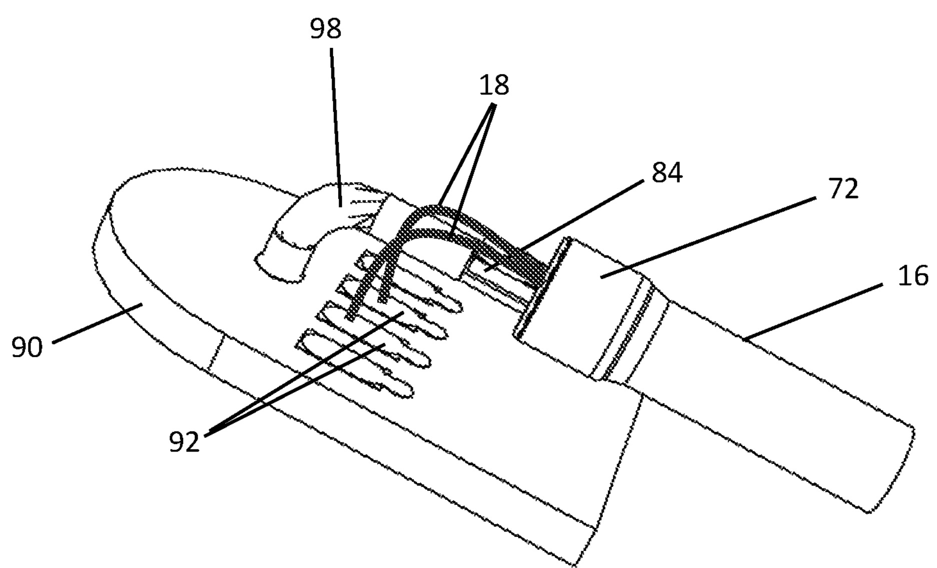
FIG. 12 shows a perspective view of a second end of the cable shown in FIGS. 1, 3A, and 5-10 including a second pipe and the wires from FIGS. 7-9 protruding from the second end of the cable with the cable attached adjacent to a cable module including a tube fitting and a cable module base.
Figure 13:
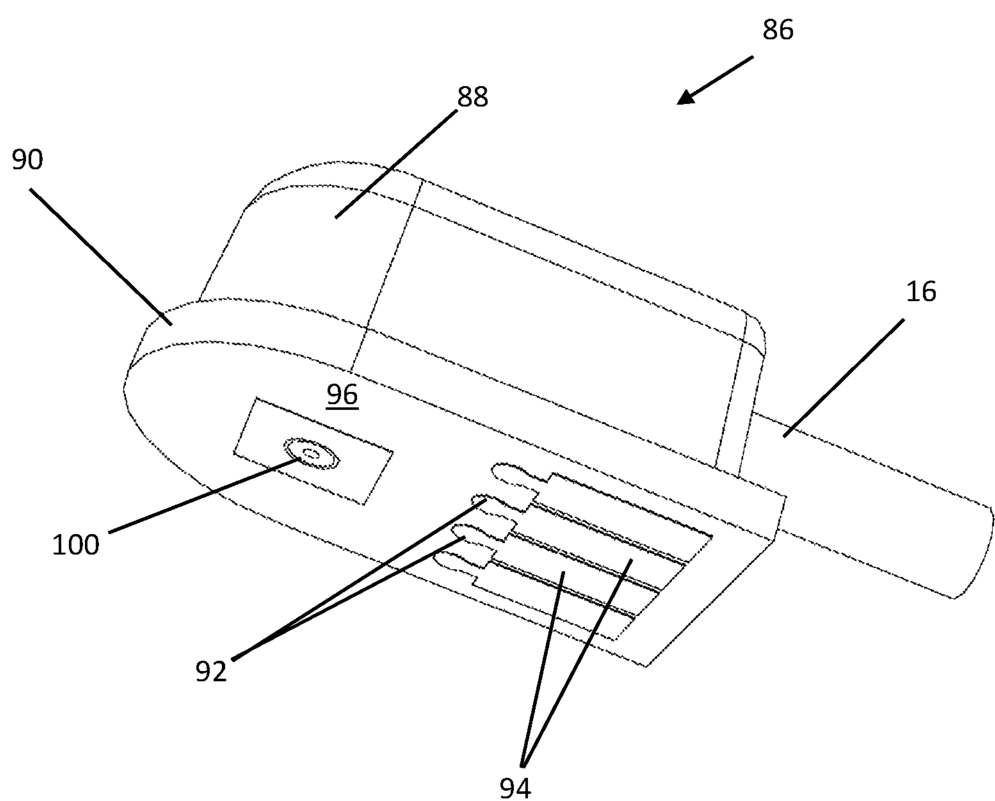
FIG. 13 shows a perspective view of the cable module from FIG. 12 including a cable module cover and other connection features along a first surface of the cable module.

FIG. 12 shows the controller end 72 of the cable 16 including a controller pipe 84 extending from the shroud void to outside of the controller end 72. The controller pipe 84 is preferably a small metal pipe and the remainder of the controller end 72 is substantially sealed proximate to where the controller end 72 is attached proximate to the controller board 66. Liquid resin, wax, or other suitable material can be used to seal the controller end 72. With further reference to FIGS. 12-13, the controller end 72 is preferably molded or otherwise attached proximate to a cable module 86. Other than electrical components, the cable module 86 is preferably made of plastic or other polymer-based material. The cable module 86 preferably includes a cable module cover 88 and a cable module base 90 and a first set of two or more metal electric contacts 92 extending through the base 90 to a second set of two or more electric contacts 94 located along a bottom surface 96 of the cable module base 90. The two or more wires 18 are preferably soldered at or otherwise in direct contact with the first set of electric contacts 92 so that the second set of electric contacts 94 are in electrical communication with the two or more wires 18. The cable module 86 further includes a tube fitting 98 in direct fluid communication with the controller pipe 84 and extending to an outlet port 100 preferably located along the bottom surface 96 of the cable module base 90. The cable module cover 88 is filled with e.g., liquid resin, wax, or other suitable material.

Figure 14:
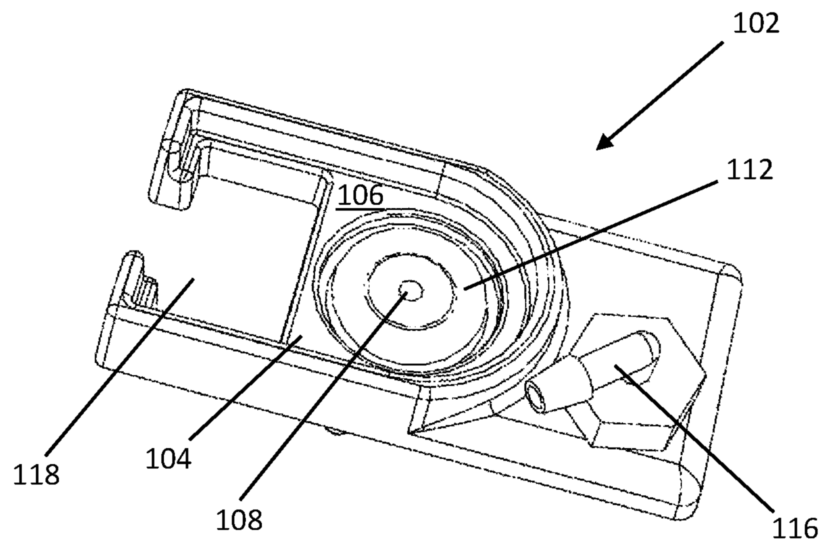
FIG. 14 shows a perspective view of a controller connector assembly configured to engage with the bottom surface of the cable module from FIGS. 12-13.
Figure 15:
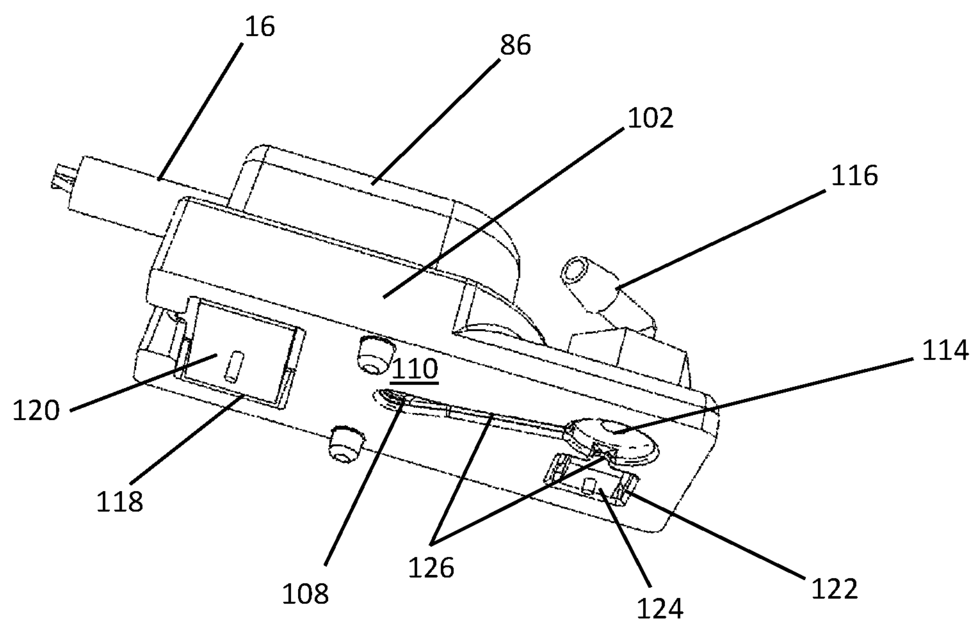
FIG. 15 shows a perspective view of the controller connector assembly and cable module from FIGS. 12-14 engaged together and further showing features including channels along a lower surface of the controller connector assembly.

With reference to FIGS. 14-15, the controller board 66 further includes a controller connector assembly 102 including a bed 104 wherein the cable module 86 is preferably shaped or otherwise configured to fit congruently in the bed 104 and physically engage with one or more other features of the controller board 66. The controller connector assembly 102 is preferably made of plastic or other polymer-based material. The bed 104 preferably includes a substantially flat base surface 106 that can fit congruently and tightly against the bottom surface 96 of the cable module base 90. The controller connector assembly 102 includes an inlet port 108 in direct fluid communication with the outlet port 100 when the cable module 86 is engaged against the bed 104 wherein the inlet port 108 extends through the bed 104 to a lower surface 110 of the controller connector assembly 102 which is preferably substantially flat. An o-ring seal 112 is preferably located around the inlet port 108 to help create a substantially air-tight seal between the outlet port 100 and the inlet port 108. A second aperture 114 preferably extends through the controller connector assembly 102 from the lower surface 110 to an air line fitting 116 attached proximate to the controller connector assembly 102.

The lower surface 110 of the controller connector assembly 102 preferably includes a first recess 118 to create space for an electrical connector 120, a second recess 122 to create space for a second pressure transducer 124 and one or more controller connector assembly channels 126 routed or otherwise located in the controller connector assembly putting the inlet port 108, the second aperture 114 (leading to the airline fitting 116), and the second pressure transducer 124 in direct fluid communication with one another when the channels 126 are closed off by an adjoining object.

Figure 16:
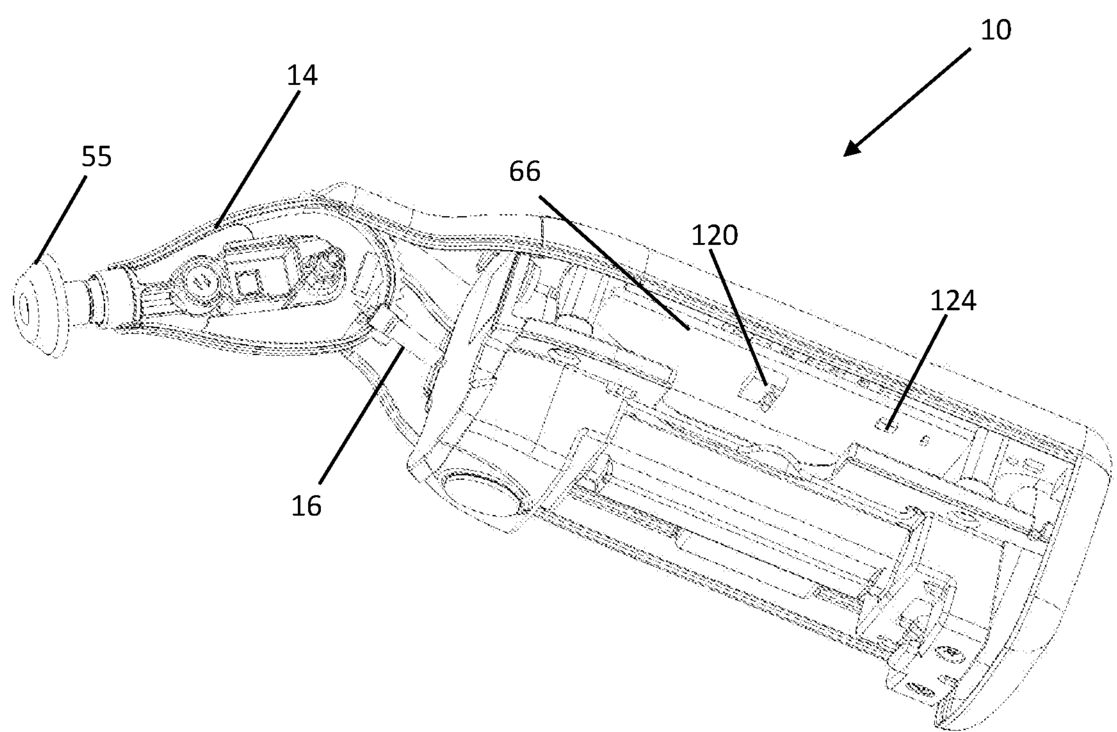
FIG. 16 shows a drawing of the audiometric instrument with the cable module and controller connector assembly removed and showing an electrical connector and a second pressure transducer attached to a printed circuit board.

With reference to FIGS. 14-16, the controller connector assembly 102 with its multiple features serves as an interface between the cable module 86 and the controller board 66. The electrical connector 120 and the second pressure transducer 124 are both attached adjacent to the controller board 66 which is further networked with other electrical components to power and operate the audiometric instrument 10. Electrical signals pass from the controller board 66 through the electrical connector 120, through the two or more electric contacts 94, along the two or more wires 18 to two or more electrical features of the probe 14. The audiometric instrument 10 and its electrical features are preferably powered by one or more batteries 130 preferably housed in the main body 12.

With regard to air flow, the audiometric device is said to have an ear canal pressurization device (ECPD; e.g., U.S. Pat. No. 8,398,562) for varying the pressure along an air flow route. Air is supplied to the air line fitting 116 from an air pressure source (e.g., air pressurization device 82) and air pressure is controlled through the one or more controller connector assembly channels 126, up through the inlet port 108 and outlet port 100 to the tube fitting 98, through the controller pipe 84, through the cable 16, through the probe pipe 74 all the way to the probe tip 42. Because the controller board 66 is attached firmly against the lower surface 110 of the controller connector assembly 102, the open side of the one or more controller connector channels 126 is closed off and the channels 126 are substantially sealed such that the inlet port 108, the second aperture 114 (leading to the air line fitting 116), and the second pressure transducer 124 are all in direct fluid communication with one another. In a less preferred embodiment, one or more tubes can be used in lieu of the controller connector channels 126 to connect the various features along the lower surface 110 of the controller connector assembly 102. In other embodiments, a combination of channels and tubes can be used.

Figure 17:
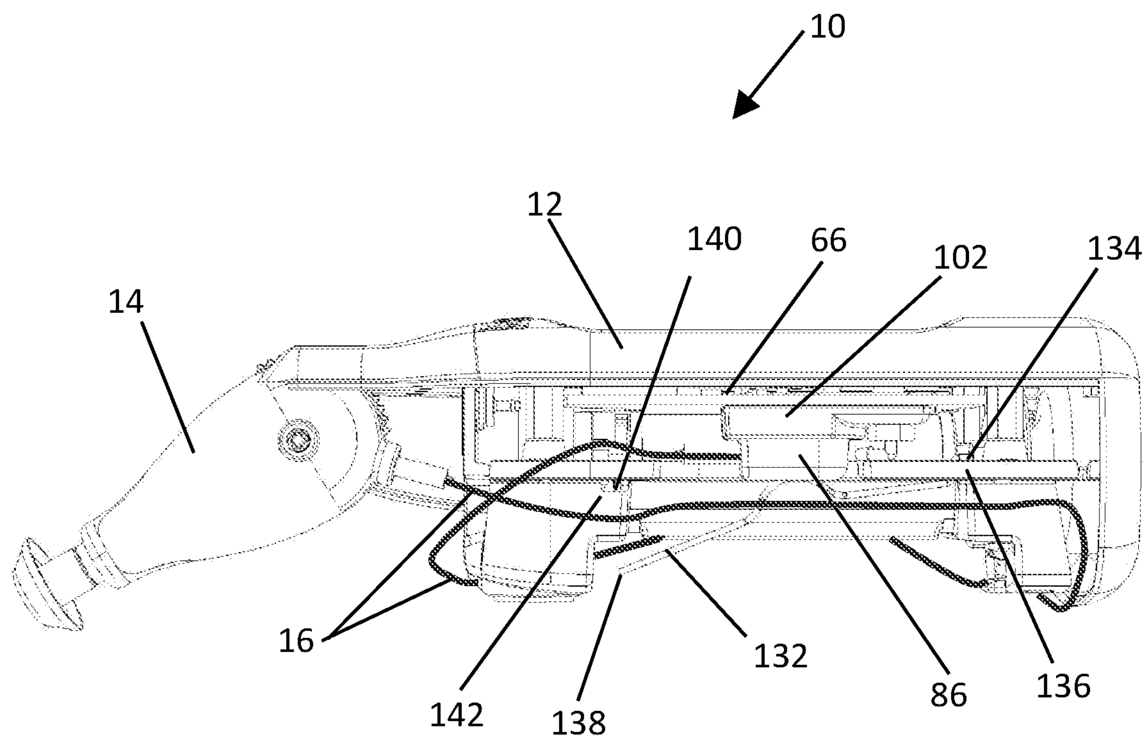
FIG. 17 shows a side view of the audiometric instrument from FIG. 1 with its outer covering removed to expose features inside of the main body.
Figure 18:
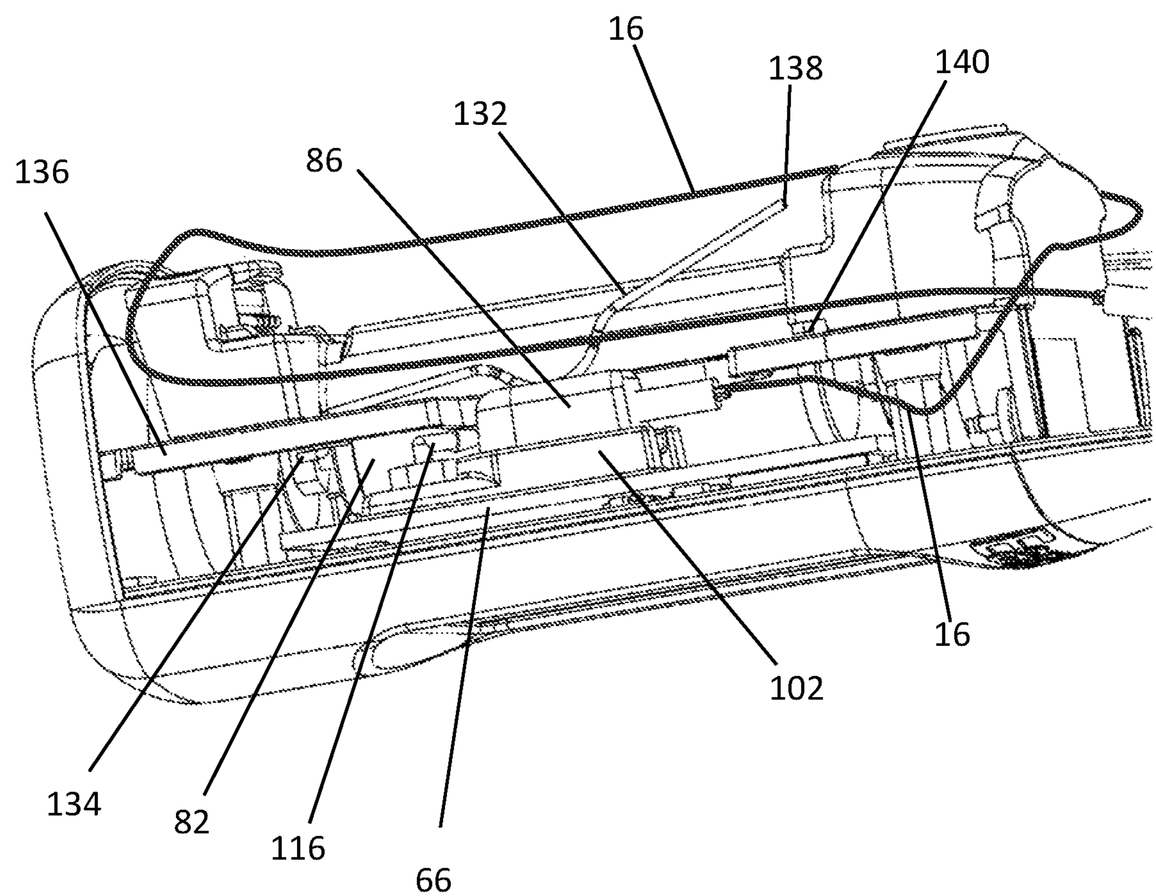
FIG. 18 shows a perspective partial view of the audiometric instrument from FIG. 1 and FIG. 17 with its outer covering removed to expose features inside of the main body.

With reference to FIGS. 1, 17 and 18, all of the features of the controller board 66 are preferably located within the main body 12 housing. The main body 12 preferably includes an engagement member 132 (e.g., a spring) that can be engaged against the cable module 86 to hold the cable module 86 tight against the bed 104 of the controller connector assembly 102, ensuring solid contact between the electrical connector 120 and the two or more electric contacts 94 as well as ensuring a good seal between the outlet port 100 and the inlet port 108. In the embodiment shown, the engagement member 132 is in the form of a spring that is preferably bent at a first end 134 and extends through a first section 136 of the main body 12. FIGS. 17 and 18 show the engagement member 132 in a disengaged state. When the engagement member 132 is engaged a second end 138 of the engagement member 132 is slid in a notch 140 at a second section 142 of the main body 12. The engagement member 132 can be disengaged from the cable module 86 for easy removal of the cable module 86 from the controller connector assembly 102 by sliding the second end 138 of the engagement member 132 from the notch 140. Although a spring is specifically mentioned, other structures known to a person having ordinary skill in the art can be used to hold the cable module 86 in place. For example, a track and groove configuration is contemplated wherein the cable module 86 can be slid into place and held against the controller connector assembly 102. The electrical connector 120 is also preferably biased outward via spring bias or other known physical biasing techniques for electric connectors.

In certain embodiments, no air or air pressure control is necessary and only electrical connections are needed between the controller board 66 and the probe 14. In those embodiments, the features related to air flow and pressure control can be left out so that the alternative audiometric instrument 10 has no air or air pressure control components. For such embodiment, there is no need to substantially seal any components.

In certain other embodiments, the cable 16 includes an air tube extending from the controller pipe 36 to the probe pipe 26 inside the shroud 68. This embodiment would obviate the need to seal the probe end 70 and the controller end 72 of the cable 16.

Figure 19:
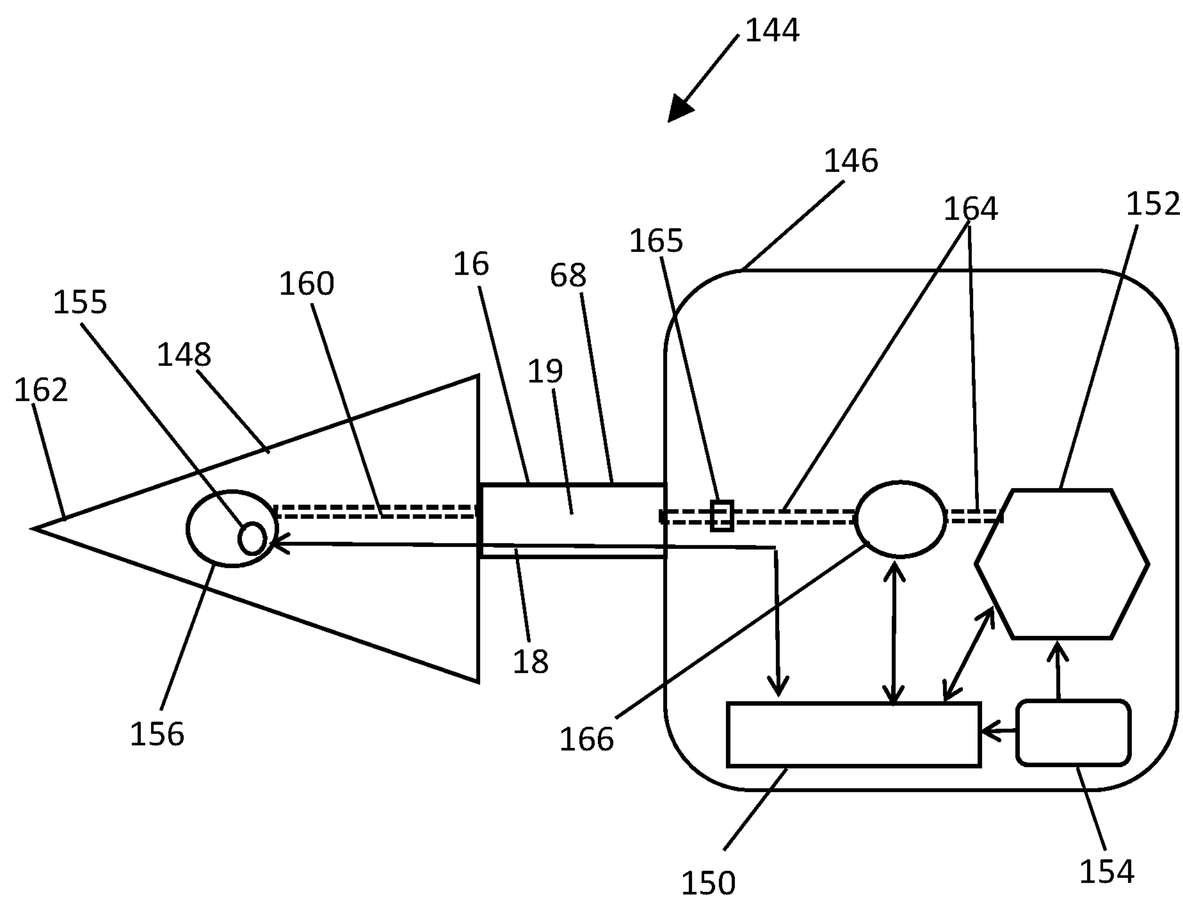
FIG. 19 shows schematic view of an audiometric instrument.

In a more general embodiment shown schematically in FIG. 19 without the specific limitations set forth above in other embodiments, an audiometric instrument 144 is disclosed including a main body 146 and a probe 148. The main body 146 includes a controller board 150 and an air pressurization device 152 which is controlled by the controller board 150. The audiometric instrument 144 is preferably powered by a battery 154, but other sources of power are also considered a part of this disclosure. The probe 148 includes electronic features 156 such as, for example, a first pressure transducer 155, one or more other transducers or speakers as discussed previously, and a microphone that are in electrical communication with the controller board 150 wherein such electrical communication is shown by arrows in FIG. 19 similar to FIG. 11. These features are also in direct fluid communication with the air pressurization device 152 via one or more channels as described herein and/or conventional tubes (referred to alternatively or collectively herein as a first conduit 160). Air flow pathways in FIG. 19 are designated by dashed lines similar to FIG. 11. The main body 146 is functionally connected to the probe 148 via the cable 16 described above which includes wires 18 for connecting the controller board 150 to the electrical features 156 of the probe 148 and a void space 19 within the shroud 68 through which air can flow from the air pressurization device 152 to the cable 16 via a tube or other conduit, then through channels and/or tubes in the probe 148 to a probe tip 162. The air pressurization device 152 is connected to the cable 16 via a second conduit 164 (one or more channels formed in a solid structure and/or one or more conventional tubes). An important novel aspect of this embodiment is the cable 16 which does not include a separate air tube but relies on the void space inside the shroud through which air can pass.

There are multiple advantages that flow from the embodiments described herein. A first advantage is found in a cable 16 that provides air flow and electricity for an audiometric instrument 10 from a controller board 66 to a probe 14 but that does not include a separate air tube which are prone to kinking. Two or more electrical wires 18 located in the shroud 68 of the cable 16 provide some rigidity which further minimizes the risk of the cable 16 kinking and cutting off air flow. Another advantage is the space saved in the instrument 10 by not using an air tube inside the cable 16.

In another aspect, space is advantageously conserved by use of controller connector assembly channels 126 along the lower surface 110 of the controller connector assembly 102 instead of using one or more tubes which are much more bulky and are prone to kinking, wear and cracking.

Yet another advantage is found in an audiometric instrument 10 wherein the cable 16 to the controller board 66 can be easily engaged and disengaged via a cable module 86 and controller connector assembly 102. Because the two or more wires 18 along the cable 16 are not soldered to the controller board 66, the cable 16 and, if necessary, the probe 14 can be switched out for a different cable and/or probe if there is a malfunction caused by the first cable 16 or the probe 14.

One novel feature of the audiometric probe described above is the use of both a first pressure transducer 38 in the probe located proximate to the probe tip 42 (and, therefore, proximate to the ear canal of a user when the probe 14 is in use) and a second pressure transducer 124 located proximate to the pressurization device 82 in the main body 12 for accurately controlling and maintaining ear canal pressure, or fixed ear canal air pressure in an audiometric immittance system. An air flow restriction 165 (narrowing or partial obstruction of an air flow line) is provided somewhere between the first pressure transducer 38 and the second pressure transducer 124. The restriction can be accomplished by reducing the cross-sectional area in a section of the core probe body channel 26 or the controller connector assembly channels 126. Alternatively, a short pipe with internal cross-sectional area smaller than the cross-sectional area of a channel in direct fluid communication with the first pressure transducer 38 and the second pressure transducer 124 may be used as the restriction. Optionally, an acoustic fused mesh dampener may be used as the restriction. Because of the restriction, pressure changes in a user's ear canal (proximate to the first pressure transducer 38) at a slightly slower rate than pressure changes at the pressure source (proximate to the second pressure transducer 124). By knowing the cross-sectional area, or the acoustic resistance of the mesh dampener, better comparative control calculations can be made using data from the first pressure transducer 38 and the second pressure transducer 124.

In one aspect, the dual pressure transducer configuration provides the capability to continually monitor for an air leak around the cuff of the probe tip 42 by comparing ear canal pressure readings from the first pressure transducer 38 with pressure readings from the second pressure transducer 124 near the pressure control source wherein such readings are specifically corrected/adjusted based on the restriction located between the two pressure transducers. The controller board 66 may include one or more processors to receive pressure readings from the first pressure transducer 38 and the second pressure transducer 124 in order for the controller board to take different optional actions including changing the pressure in the audiometric probe by adjusting output from the pressurization device 82. Using the controller board 66, a control loop using automatic gain control (AGC) can be used to maintain or vary the air pressure in the audiometric instrument and in the ear canal of a user.

In another aspect, the dual pressure transducer configuration allows for more stringent pressure control since air system automatic gain control (AGC) can be referenced to the second pressure transducer 124 (close to the pressure control source) to minimize delays due to the length of the air flow path between the pressure control source and the first pressure transducer 38. Additionally, more precise coordination of AAI measures to the ear canal pressure can be ensured by using the pressure readings from the first pressure transducer 38 which is close to the ear canal of a user.

In yet another aspect, the dual pressure transducer configuration provides an additional layer of safety for a user since pressure readings are available from two independent sources in two separate locations within the audiometric instrument 10. If a sudden pressure change were to occur near the pressurization source (e.g., the pressurization device 82) due to a malfunction or mechanical failure, corrective action could be taken before the pressure change reaches the ear canal of a user.

Although the audiometric instrument 10 described above has various novel features, the dual pressure transducer configuration including the restriction between transducers can be employed in an audiometric instrument with more conventional features. For example, in FIG. 19, the electrical features 156 can include a first pressure transducer 155 located proximate to the probe tip 162 and a second pressure transducer 166 can be located proximate to the air pressurization device 152 including a restriction 165 along the second conduit 164, thereby providing the dual pressure transducer configuration with the various benefits described above. In a related embodiment with dual pressure transducer configuration, the audiometric instrument 144 shown in FIG. 19 may include an air tube located in the cable similar to conventional cables which connects the first conduit 160 with the second conduit 164. In this alternative embodiment, a restriction can be included in the air tube instead of in the second conduit 164.

Figure 20:
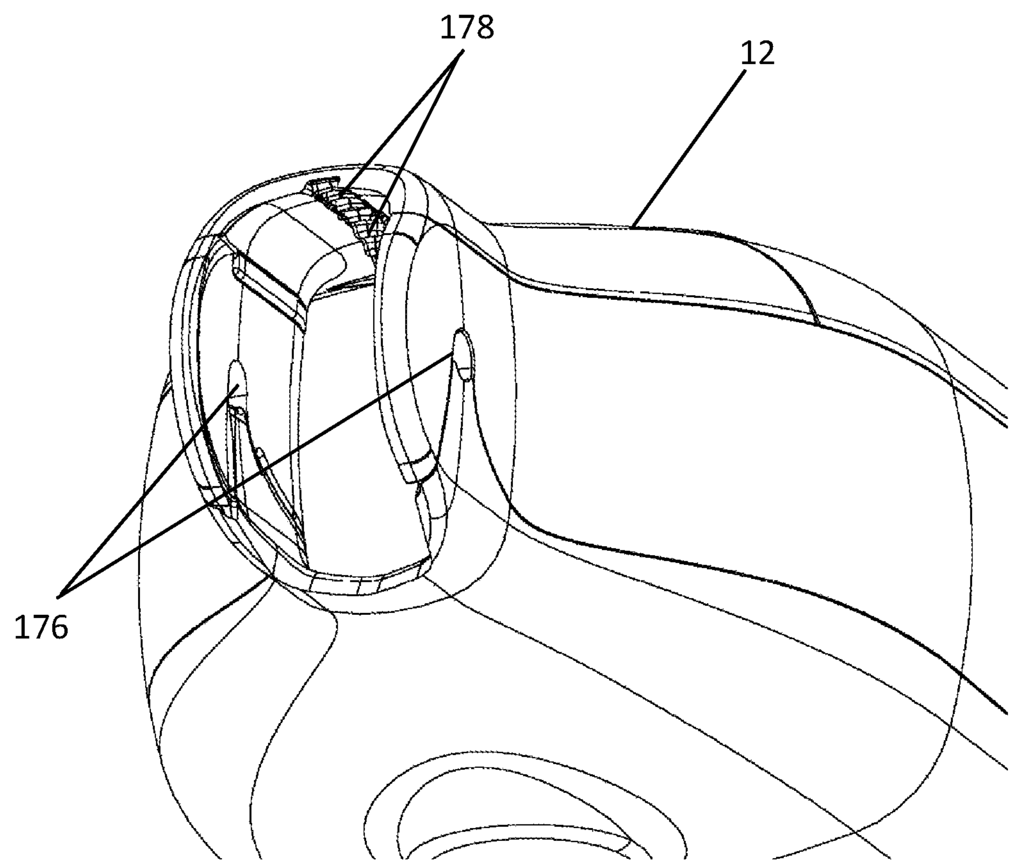
FIG. 20 shows a perspective view of a portion of the main body of the audiometric instrument shown in FIG. 1.

Another novel aspect of the apparatuses and methods described herein includes the outer physical structure of the audiometric probe 14 which includes a rounded rear surface 168 including a plurality of protrusions 170 as shown, for example, in FIG. 6A. The probe 14 preferably includes lateral extensions 172 (preferably in the form of one or more screws to hold the outer casing 64 together), which extend laterally from the probe outer casing 64. With reference to FIG. 20, these features allow the probe 14 to removably engage with a pair of internal grooves 176 in the main body 12 of audiometric instrument 10 in a hinge configuration so that the probe 14 can preferably rotate relative to the main body 12 along the internal grooves 176 in mating configuration with the lateral extensions 172 extending laterally from the probe casing 64. The main body 12 also preferably includes a plurality of main body indentations 178 which mechanically engage with the plurality of protrusions 170 of the probe 14 so that the probe can be rotated to different stationary positions relative to the main body 12.

Figure 21:
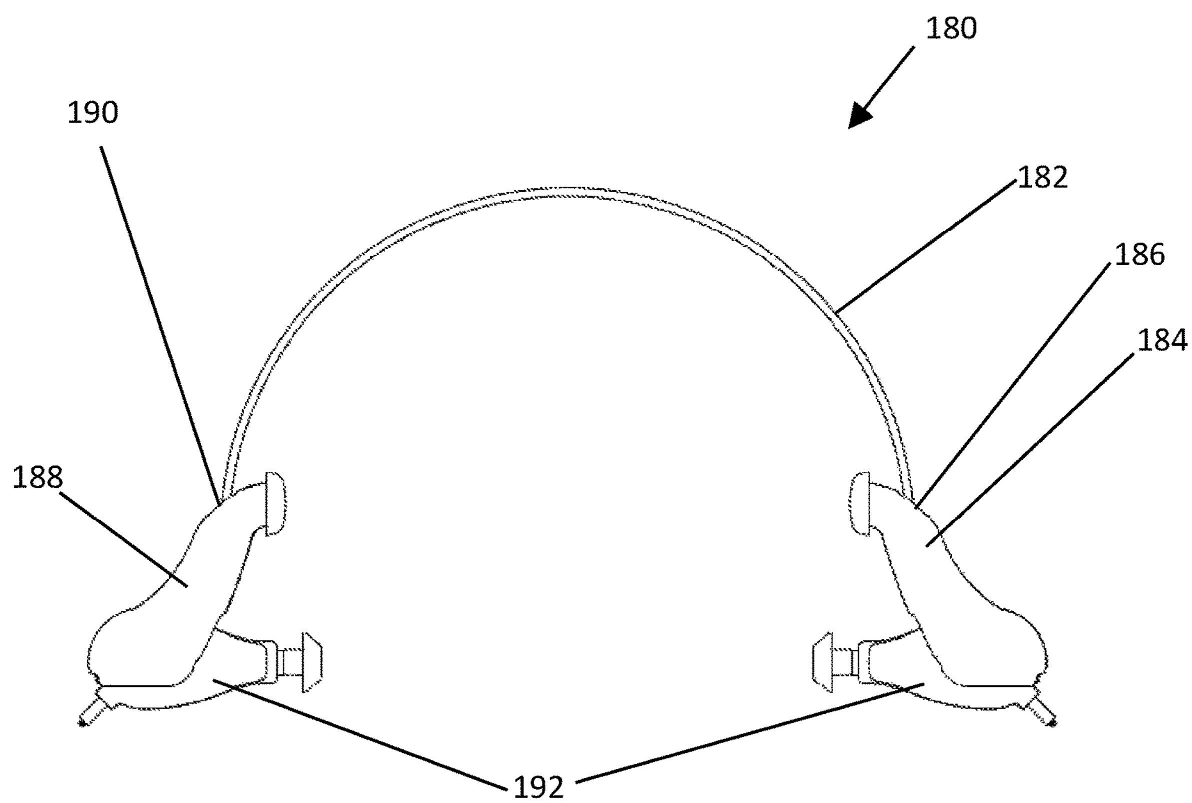
FIG. 21 shows a dual probe headset for use with an audiometric instrument controller.

Another novel aspect of the apparatuses and methods described herein include use of multiple probes such as probe 14 in a dual probe audiometric headset 180 as shown in FIG. 21. The dual probe headset is configured to be used over the head of a user for binaural audiometric testing. The headset 180 includes a headband 182 that provides inward spring tension about a user's head, a first probe holder 184 connected at or proximate to a first end 186 of the headband 182, and a second probe holder 188 connected at or proximate to a second end 190 of the headband 182. The headband 182 is preferably made of metal or other resilient material that can provide spring tension. Preferably, the headband 182 itself does not contact the head of a user but rather "floats" above the head of a user and the probes and probe holders provide two points of contact with the head of a user. The headband 182 is shaped large enough to fit around heads of any size.

Figure 22:
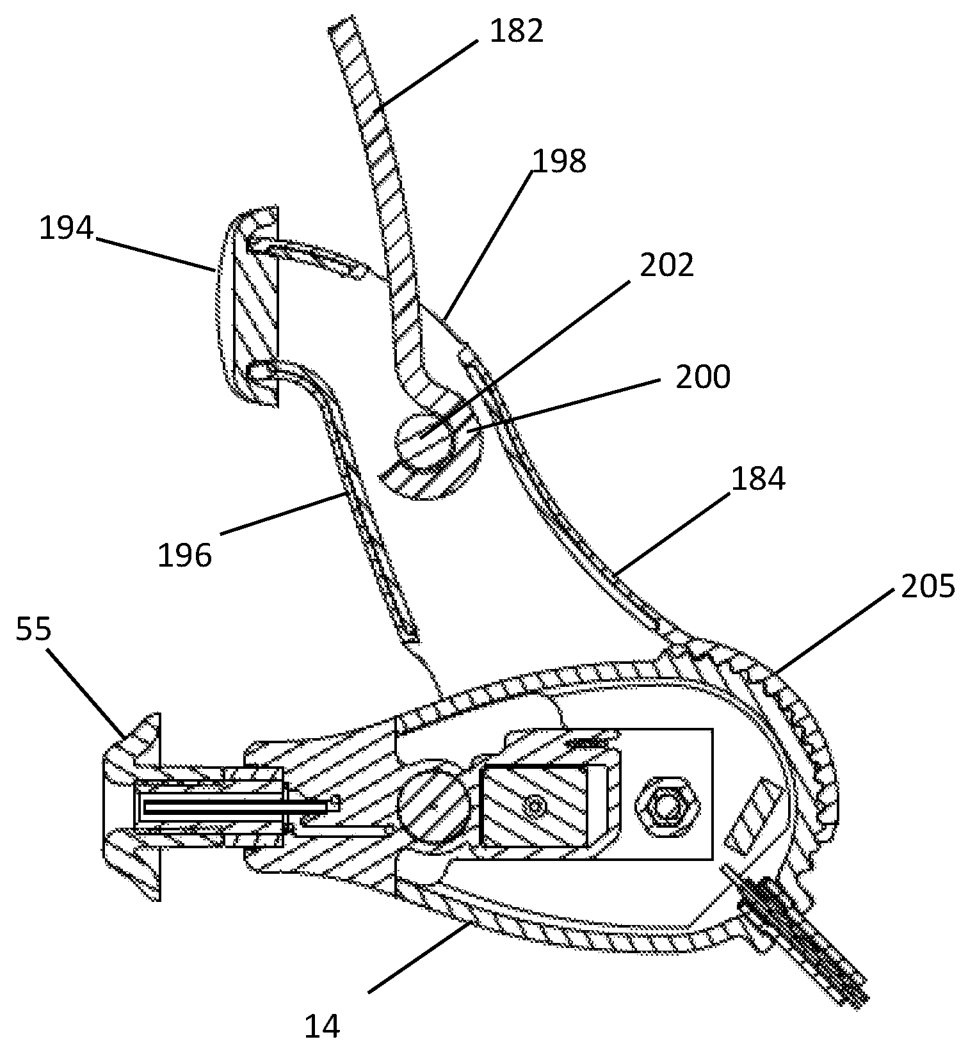
FIG. 22 shows a cross-sectional view of a first probe holder connected to a headband and an audiometric probe.

FIG. 22 shows a cross-sectional view of the first probe holder 184 and a probe such as, for example, probe 14 from FIGS. 2-6, attached to the first probe holder 184. The first probe holder 184 includes a pad 194 and a pad arm 196. There is a pad arm aperture 198 located along the pad arm 196 through which the first end 186 of the headband 182 can be inserted. The pad arm aperture 198 is preferably long and narrow to permit movement along only one axis. The first end 186 of the headband 182 includes a hook 200 which fits partially around a hook catch cylinder 202 extending across the interior of the pad arm 196. Because of the size/length of the pad arm aperture 198, enough room is provided for the first probe holder 184 to move and swivel relative to the headband 182.

Figure 23:
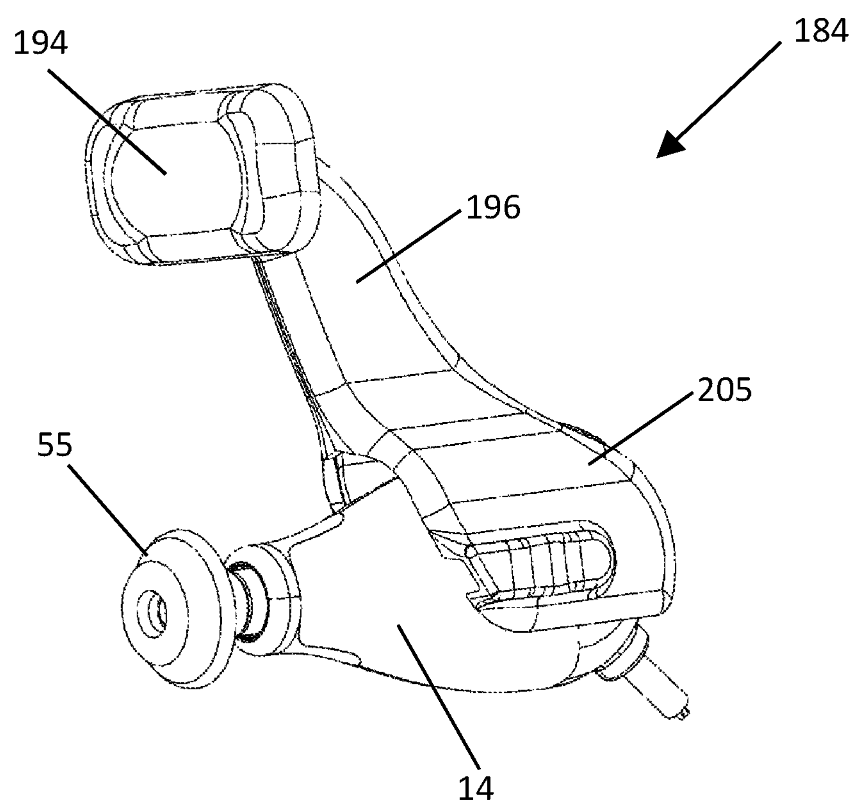
FIG. 23 shows a perspective view of the first probe holder and associated audiometric probe from FIG. 22.
Figure 24:
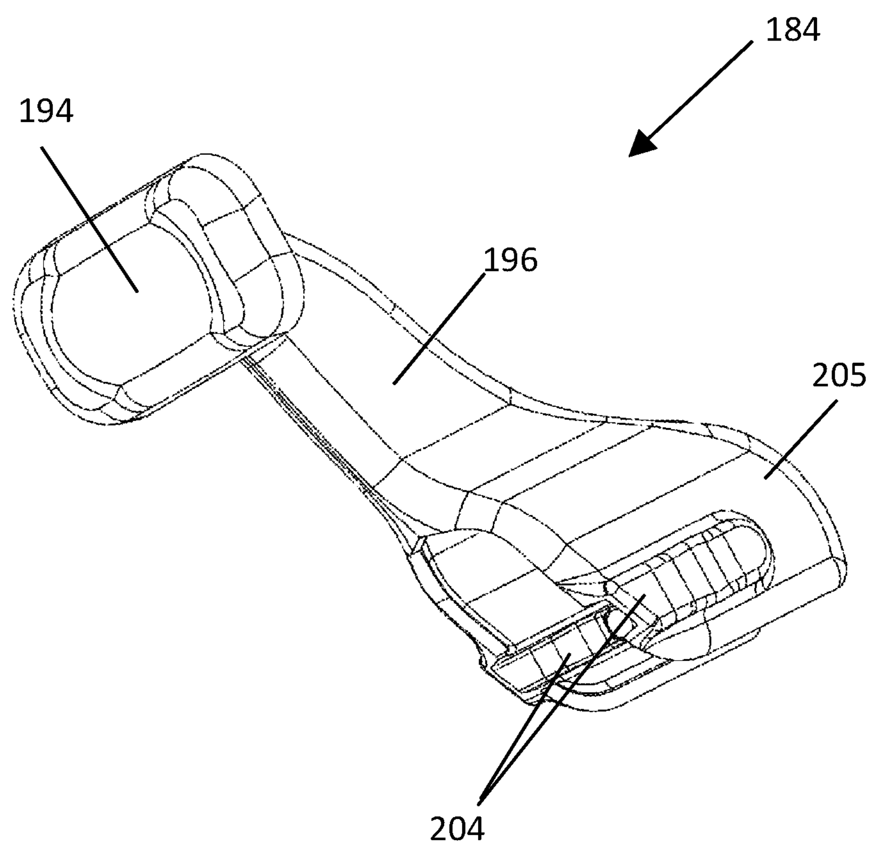
FIG. 24 shows a perspective view of the first probe holder shown in FIG. 22 and FIG. 23.
Figure 25:
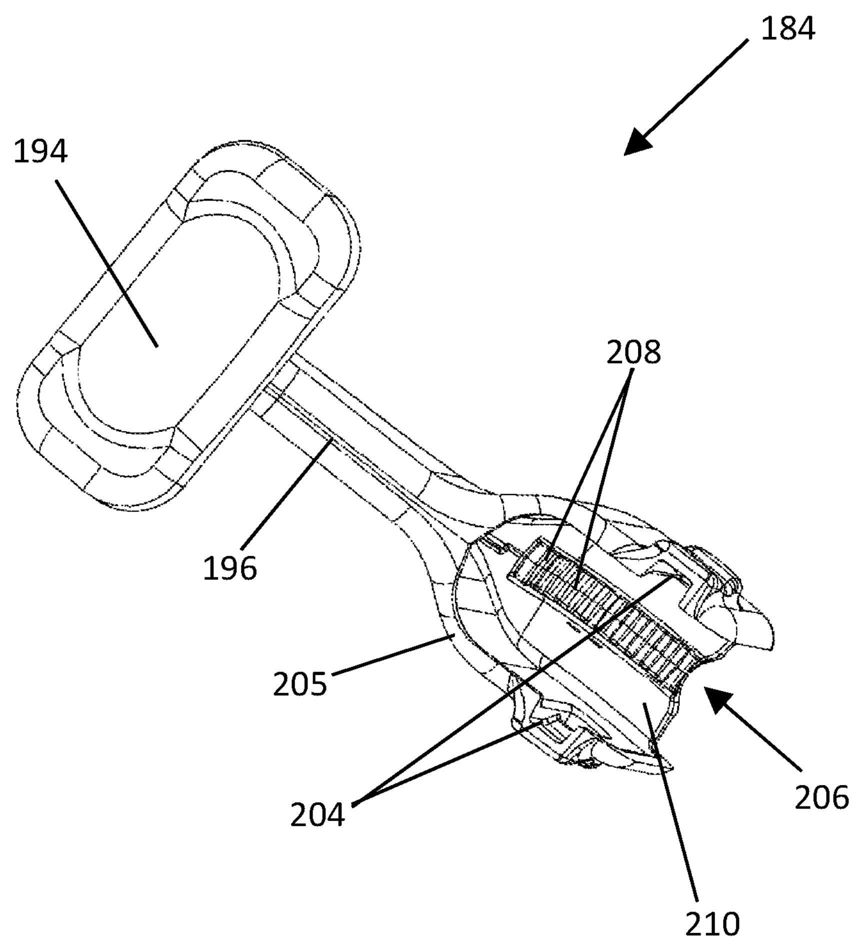
FIG. 25 shows a different perspective view of the first probe holder shown in FIG. 24.
Figure 26:
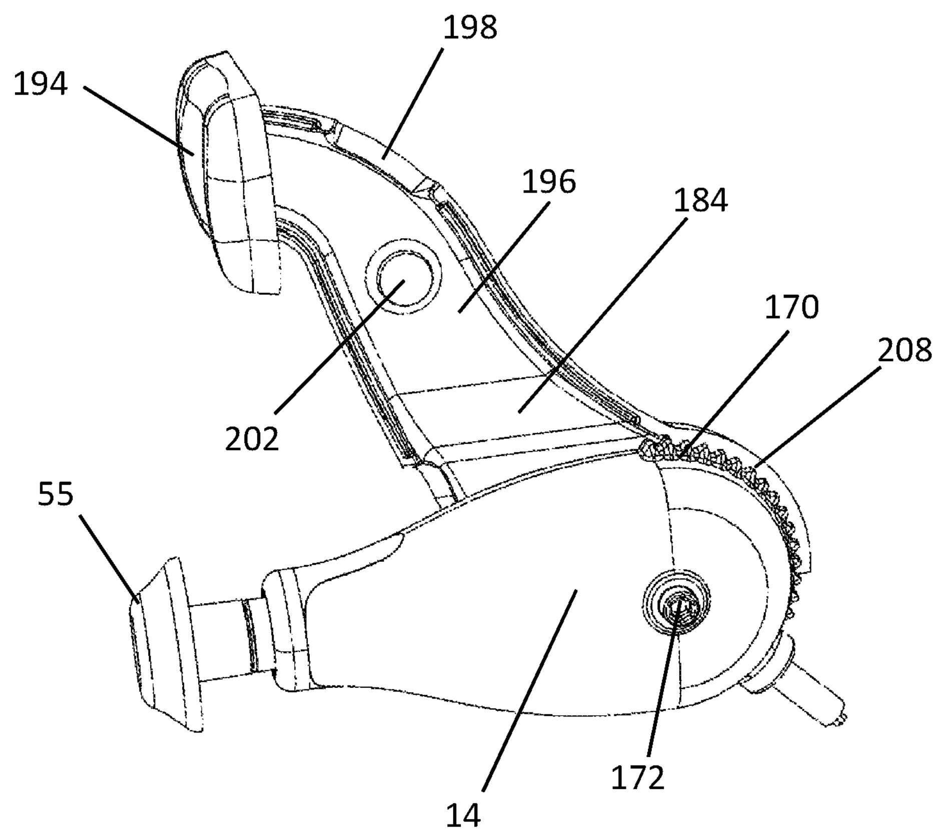
FIG. 26 shows a partial cross-sectional view of the first probe holder shown in FIG. 23 along with a full view of the attached probe.

FIG. 23 shows a perspective view of a probe holder (e.g., first probe holder 184) including a probe (e.g., probe 14) engaged with the first probe holder 184. FIG. 24 shows a perspective view of the first probe holder 184 showing probe holder grooves 204 in which the lateral extensions 172 extending laterally from the probe casing 64 of the probe 14 are inserted for removable attachment to the first probe holder 184. FIG. 25 shows a different perspective view of the first probe holder 184 showing a shell 205 defining a primary cavity 206 in which the rounded rear surface 168 of the probe 14 is inserted to engage the plurality of protrusions 170 with a plurality of probe holder indentations 208 along an inner surface 210 of the shell 205. Because of the engagement of the protrusions 170 with the probe holder indentations 208 as shown in FIG. 26, the probe 14 can be rotated about the lateral extensions 172 relative to the first probe holder 184 to various stationary positions, thereby providing angle selection to accommodate a wide range of head sizes. More specifically, this feature allows for users with different sized anatomical features to use the same dual probe headset 180. The swivel connection between the headband 182 and the first probe holder 184 provides additional flexibility for users with different sized/shaped anatomical features. Additionally, probe holders and other associated parts can be 3D printed in various sizes to further broaden the range of persons that can comfortably and effectively use an audiometric device including the dual probe headset described herein.

Another important feature of each probe holder described herein is the inclusion of the pad arm 196 and the pad 194 distal from the probe 14 attached to the probe holder 184. With the inclusion of the pad 194, the first probe holder 184 and the probe 14 have a 2-point contact balance along the head of a user wherein the pad 194 acts as a fulcrum and the spring tension from the headband pressing at a point on the probe holder 184 below the pad 194 (i.e., at the hook catch cylinder 202) drives or otherwise rotates an ear cuff 55 of the probe 14 into the ear of a user. Proper placement of the fulcrum point with respect to the pad 194 ensures that most of the inward spring force is made against the head through the pad 194, providing for stable positioning, keeping the headset 180 from rotating about the head of a user. The ear cuff 55 on the probe 14 acts as the second point of contact of the probe/probe holder on the head of a user. The width of the pad 194 and two points of contact prevent the angle of the probe 14 from shifting as would occur with a stethoscope which has only a single point of contact with a user's concha. The other side of the dual probe headset 180 including the second probe holder 188 mirrors the first side and a uniform force is thereby applied to both probe holders and probes 192 to seal each probe in the conchae of the user of the headset 180. Most of the headband 182 spring tension is distributed to the pads (e.g., pad 194). As such, head movement by a user does not interfere with the placement of the probes 192. Some of the spring tension is also distributed to the probes 192 which helps ensure that there is enough pressure on the probes 192 to form a substantially airtight seal with the ears of a user.

Figure 27:
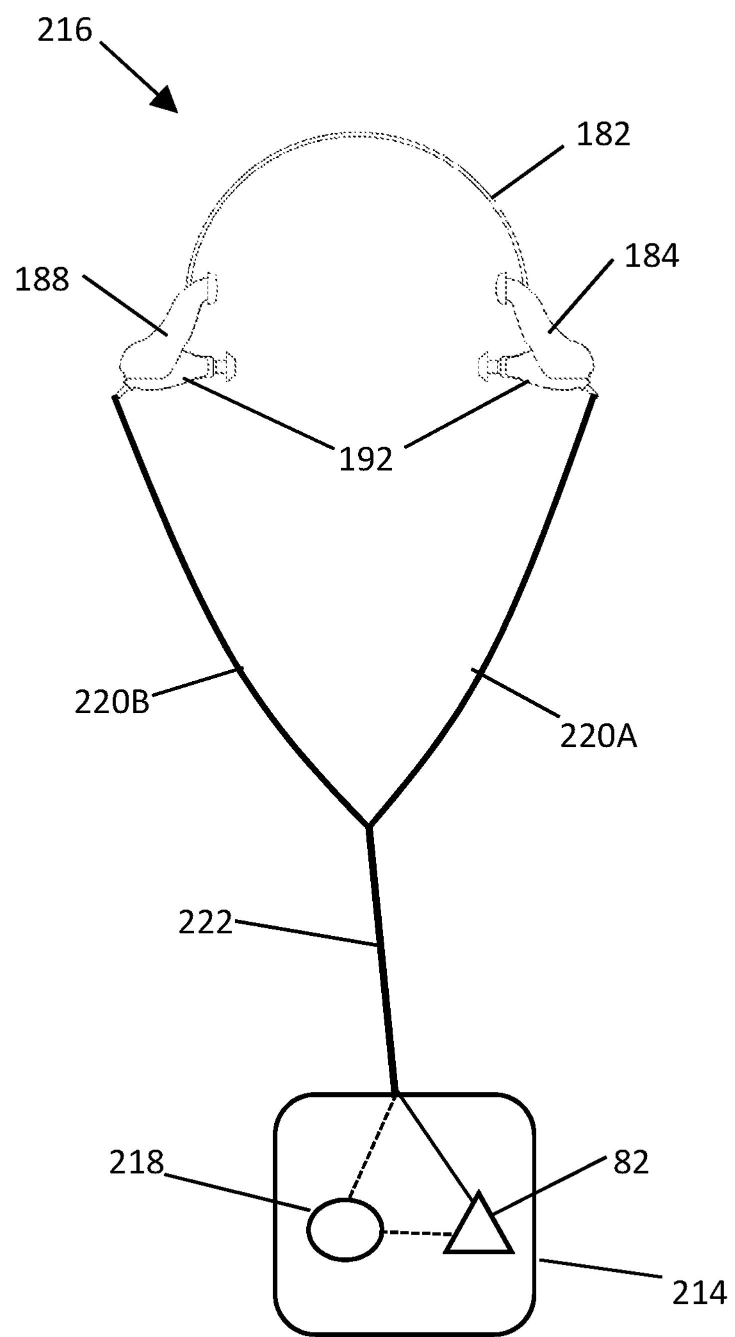
FIG. 27 shows a schematic drawing of an audiometric instrument including a dual probe headset.

The probes 192 in the dual probe headset 180 are preferably connected to the same control device (e.g., controller board 66) as a single audiometric instrument. Although the main body 12 of the audiometric instrument 10 described above includes certain specific features, the dual probe headset 180 and associated probes 192 can be used in tandem with a different main body 214 of an audiometric instrument 216 schematically shown in FIG. 27 with similar but different features than the main body 12 of the audiometric instrument 10 described above. In various embodiments, the probes 192 are connected to a control device 218 via cables (first cable 220A and second cable 220B) wherein the cables operate similarly to or identically to the cable 16 previously described herein and are preferably in electrical communication with the control device 218 and in direct fluid communication with an air pressurization device 82 connected to the main body 214. The first cable 220A and second cable 220B can be physically joined at a certain point along the length of the cables, thereby forming a "V" configuration. Alternatively, the first cable 220A and second cable 220B can be physically joined at a certain point along the length of the cables, thereby forming a "Y" configuration as shown in FIG. 27. The air flow portions of the cables 220 are joined together and sent down a base cable 222 in the same airflow space. Any associated electrical wiring from the first cable 220A and the second cable 220B also extends down the base cable 222. The weight of the cables 220 acts as a weight to balance the headset 180 rotationally about the head of a user regardless of whether the cables 220 fall along a user's chest or a user's back. The control device 218 can be located at the base of the "Y" configuration and attached at a distal end of the base cable in electrical communication with the probes 192.

The probes 192 preferably include all of the features of probe 14 described above providing many advantages for the dual probe headset 180. For example, with these features, an audiometric device including the dual probe headset 180 with dual probes 192 is capable of conducting binaural audiometric testing with masking. Each probe can independently present pure tone, noise or speech signals. The microphone in each probe (i.e., microphone 52) can be used to monitor the sound in each ear of the user of the audiometric instrument 216 and sound levels may be verified independently in each ear canal. Each probe preferably includes ear canal pressurization (ECPD) capability (e.g., air pressurization device 82 as described previously herein) for aural acoustic immittance testing. The dual speakers (first transducer 34 and second transducer 40) in each probe allow for binaural otoacoustic emission (OAE) testing. The relative weight of the dual probe headset 180 is also advantageous because it is lighter than conventional TDH-39 audiometric headsets.

Although specific examples and combinations of features have been described, various other embodiments including different combinations of the various features described herein are considered a part of this disclosure. The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A dual audiometric probe headset comprising:

a. a resilient headband including a first end and a second end;

b. a pair of audiometric probe holders including a first probe holder attached proximate to the first end of the headband and a second probe holder attached proximate to the second end of the headband, each probe holder comprising;

i. a shell defining a primary cavity for docking an audiometric probe in the primary cavity and attaching an audiometric probe to the probe holder;

ii. a pad located at a first end of the probe holder for resting the probe holder against the head of a user of the headset;

iii. a pad arm extending from the shell to the first end of the probe holder.

2. The dual audiometric probe headset of claim 1 further comprising a pair of probes including a first audiometric probe docked in the primary cavity of the first probe holder and attached to the first probe holder and a second audiometric probe docked in the primary cavity of the second probe holder and attached to the second probe holder.

3. The dual audiometric probe headset of claim 2 wherein the first probe holder further comprises a first pair of probe holder grooves, wherein the second probe holder further comprises a second pair of probe holder grooves, wherein the first audiometric probe further comprises a first pair of lateral extensions mechanically engaged with the first pair of probe holder grooves, and wherein the second audiometric probe further comprises a second pair of lateral extensions mechanically engaged with the second pair of probe holder grooves.

4. The dual audiometric probe headset of claim 2 wherein each audiometric probe comprises a plurality of substantially equally spaced protrusions oriented along an outer surface of each audiometric probe and wherein each probe holder further comprises a plurality of substantially equally spaced indentations inside the primary cavity of each probe holder along an inner surface of each probe holder wherein the plurality of protrusions mechanically engage with the plurality indentations so that the first audiometric probe can be selectively adjusted to different stationary positions relative to the first probe holder and the second audiometric probe can be selectively adjusted to different stationary positions relative to the second probe holder.

5. The dual audiometric headset of claim 2 further comprising a first cable, a second cable and a main body including a controller wherein the first probe is connected to and in electrical communication with the controller via the first cable and wherein the second probe is connected to and in electrical communication with the controller via the second cable.

6. The dual audiometric headset of claim 5 wherein the main body further comprises an air pressurization device in electrical communication with the controller and wherein the first probe is in direct fluid communication with the air pressurization device via the first cable and wherein the second probe is in direct fluid communication with the air pressurization device via the second cable.

7. The dual audiometric headset of claim 2 further comprising a first cable, a second cable, a base cable and a main body wherein the first cable and the second cable are jointly connected proximate to a first end of the base cable, and wherein the main body is attached proximate to a second end of the base cable, the main body including a controller wherein the first probe is connected to and in electrical communication with the controller via the first cable and base cable and wherein the second probe is connected to and in electrical communication with the controller via the second cable and the base cable.

8. The dual audiometric headset of claim 2 wherein the headband is larger than the head of a large adult human so that the only physical contact between the dual audiometric headset and the head of a user is via the probe holder pads and the pair of probes, with the probe holder pads preventing the dual audiometric headset from rotating on the head of a user.

9. The dual audiometric headset of claim 8 wherein the resilient headband provides spring tension to force the probe holder pads and the pair of probes against the head of a user to form a substantially airtight seal with the ears of a user.

10. The dual audiometric headset of claim 9 wherein the headband is attached to specific locations along the pad arms so that more than 50% of the force exerted by the dual audiometric headset on the head of a user is exerted through the pads.

11. The dual audiometric probe headset of claim 1 wherein the first end of the headband further comprises a hook shape for attaching the headband to the first probe holder and wherein the second end of the headband further comprises a hook shape for attaching the headband to the second probe holder.

12. The dual audiometric probe headset of claim 11 wherein each probe holder further comprises a pad arm aperture through which an end of the headband can be inserted and a substantially cylindrical hook catch cylinder located inside the pad arm wherein the hook shaped first end of the headband is connected to and partially around the hook catch cylinder of the first probe holder, and wherein the hook shaped second end of the headband is connected to and partially around the hook catch cylinder of the second probe holder.

13. The dual audiometric probe headset of claim 12 wherein the pad arm aperture of the first probe holder is a long and narrow aperture long enough to permit the first probe holder to rotate about the hook catch cylinder of the first probe holder relative to the hook shaped first end of the headband, and wherein the pad arm aperture of the second probe holder is a long and narrow aperture long enough to permit the second probe holder to rotate about the hook catch cylinder of the second probe holder relative to the hook shaped second end of the headband.

14. The dual audiometric headset of claim 1 wherein the pad provides a large surface area for contact with the head of a user, such surface area ranging in size from at least 6 $cm^2$ to about 10 $cm^2$.

* * * * *